US012611453B2

(12) United States Patent
Geleziunas et al.

(10) Patent No.: US 12,611,453 B2
(45) Date of Patent: Apr. 28, 2026

(54) METHOD OF INDUCING AN HIV-1-SPECIFIC IMMUNE RESPONSE USING A CHIMPANZEE ADENOVIRUS VECTOR ENCODING AN HIVACAT T-CELL IMMUNOGEN AND TLR7 AGONIST

(71) Applicant: Gilead Sciences, Inc., Foster City, CA (US)

(72) Inventors: Romas Geleziunas, Belmont, CA (US); Devi Sengupta, San Francisco, CA (US); Christian Brander, Tiana (ES); Beatriz Mothe Pujadas, Tiana (ES); Ian McGowan, Barcelona (ES)

(73) Assignee: Gilead Sciences, Inc., Foster City, CA (US)

(*) Notice: Subject to any disclaimer, the term of this patent is extended or adjusted under 35 U.S.C. 154(b) by 1121 days.

(21) Appl. No.: 17/610,040

(22) PCT Filed: May 21, 2020

(86) PCT No.: PCT/US2020/033959
§ 371 (c)(1),
(2) Date: Nov. 9, 2021

(87) PCT Pub. No.: WO2020/237027
PCT Pub. Date: Nov. 26, 2020

(65) Prior Publication Data

US 2022/0218711 A1 Jul. 14, 2022

Related U.S. Application Data

(60) Provisional application No. 62/851,363, filed on May 22, 2019.

(51) Int. Cl.

| | |
|---|---|
| ***A61K 39/21*** | (2006.01) |
| ***A61K 31/519*** | (2006.01) |
| ***C12N 7/00*** | (2006.01) |
| ***C12N 15/86*** | (2006.01) |
| *A61K 39/00* | (2006.01) |

(52) U.S. Cl.
CPC ............ *A61K 39/21* (2013.01); *A61K 31/519* (2013.01); *C12N 7/00* (2013.01); *C12N 15/86* (2013.01); *A61K 2039/5256* (2013.01); *A61K 2039/54* (2013.01); *A61K 2039/545* (2013.01); *C12N 2710/10332* (2013.01); *C12N 2710/10341* (2013.01); *C12N 2710/10362* (2013.01)

(58) Field of Classification Search
CPC .................. A61K 39/21; A61K 31/519; C12N 2710/10341; C12N 2710/16034
See application file for complete search history.

(56) References Cited

U.S. PATENT DOCUMENTS

| | | | |
|---|---|---|---|
| 3,798,209 | A | 3/1974 | Witkowski et al. |
| 3,950,351 | A | 4/1976 | Rossignol et al. |
| 4,539,205 | A | 9/1985 | Goodman et al. |
| 4,639,436 | A | 1/1987 | Junge et al. |
| 4,643,992 | A | 2/1987 | Goodman et al. |
| 4,880,784 | A | 11/1989 | Robins et al. |
| 5,011,828 | A | 4/1991 | Goodman et al. |
| 5,041,426 | A | 8/1991 | Robins et al. |
| 5,057,540 | A | 10/1991 | Kensil et al. |
| 5,081,226 | A | 1/1992 | Berzofsky et al. |
| 5,128,319 | A | 7/1992 | Arlinghaus |
| 5,395,937 | A | 3/1995 | Nikolaides et al. |
| 5,397,781 | A | 3/1995 | Yanagibashi et al. |
| 5,424,311 | A | 6/1995 | Billhardt-troughton et al. |
| 5,554,372 | A | 9/1996 | Hunter |
| 5,620,978 | A | 4/1997 | Cai et al. |
| 5,639,854 | A | 6/1997 | Sia et al. |
| 5,681,835 | A | 10/1997 | Willson |
| 5,693,641 | A | 12/1997 | Buckman et al. |
| 5,700,635 | A | 12/1997 | Mcmichael et al. |
| 5,759,769 | A | 6/1998 | Sia et al. |
| 5,795,955 | A | 8/1998 | Sia et al. |
| 5,800,822 | A | 9/1998 | Sia et al. |
| 5,817,754 | A | 10/1998 | Sia et al. |
| 5,876,731 | A | 3/1999 | Sia et al. |
| 5,951,986 | A | 9/1999 | Sia et al. |
| 5,972,339 | A | 10/1999 | Walker |
| 5,976,541 | A | 11/1999 | Berzofsky et al. |
| 6,028,076 | A | 2/2000 | Hirota et al. |
| 6,093,400 | A | 7/2000 | Zimmerman et al. |
| 6,111,068 | A | 8/2000 | Zimmerman et al. |
| 6,174,666 | B1 | 1/2001 | Pavlakis et al. |

(Continued)

FOREIGN PATENT DOCUMENTS

| | | | |
|---|---|---|---|
| CH | 568392 | A5 | 10/1975 |
| CN | 101284810 | A | 10/2008 |

(Continued)

OTHER PUBLICATIONS

Franchini, G., and M. L. Bosch, May 1989, Genetic Relatedness of the Human Immunodeficiency Viruses Type 1 and 2 (HIV-1, HIV-2) and the Simian Immunodeficiency Virus, Annals NY Acad. Sci. 554(1):81-87.*
Fenner, F., et al., Jun. 2014, Classification and Nomenclature of Viruses, Vet. Virol. 21-38.*
Deng, S., et al., 2022, Viral Vector Vaccine Development and Application during the COVID-19 Pandemic, Microorganisms 10(1450):1-13.*
Ondondo, B., et al., Nov. 2014, Characterization of T-Cell Responses to Conserved Regions of the HIV-1 Proteome in BALB/c Mice, Clin. Vaccine Immunol. 21(11):1565-1572.*

(Continued)

*Primary Examiner* — Jeffrey S Parkin
(74) *Attorney, Agent, or Firm* — Fish & Richardson P.C.

(57) ABSTRACT

The present disclosure describes methods, compositions, and kits related to the combination of a TLR7 modulating compound and an HIV vaccine. The combination can be used in a method of treating or preventing an HIV infection in a human.

25 Claims, No Drawings

Specification includes a Sequence Listing.

(56) References Cited

U.S. PATENT DOCUMENTS 6,210,873 B1 4/2001 Sastry et al.
6,217,791 B1 4/2001 Kamakura et al.
6,265,539 B1 7/2001 Arlinghaus
6,268,391 B1 7/2001 Dickerson et al.
6,268,472 B1 7/2001 Zimmerman et al.
6,268,945 B1 7/2001 Roberts
6,294,322 B1 9/2001 Berzofsky et al.
6,299,884 B1 10/2001 Van et al.
6,329,381 B1 12/2001 Kurimoto et al.
6,376,501 B1 4/2002 Isobe et al.
6,440,422 B1 8/2002 Sutter et al.
6,452,325 B1 9/2002 Dupont
6,552,192 B1 4/2003 Hanus et al.
6,629,831 B2 10/2003 Wei et al.
6,677,349 B1 1/2004 Griesgraber
7,094,405 B1 8/2006 Berzofsky et al.
7,094,408 B2 8/2006 Franchini et al.
7,157,465 B2 1/2007 Isobe et al.
7,319,000 B1 1/2008 Sastry et al.
7,364,744 B2 4/2008 Hovanessian et al.
7,429,572 B2 9/2008 Clark
7,521,454 B2 4/2009 Isobe et al.
7,569,228 B2 8/2009 Howley et al.
7,592,326 B2 9/2009 Karaolis
7,612,173 B2 11/2009 Abrecht et al.
7,642,350 B2 1/2010 Pryde
7,815,916 B1 10/2010 Chang et al.
7,820,786 B2 10/2010 Thomson et al.
7,968,544 B2 6/2011 Graupe et al.
7,981,430 B2 7/2011 Hanke et al.
7,993,651 B2 8/2011 Hanke et al.
8,000,900 B2 8/2011 Heckerman et al.
8,021,669 B2 9/2011 Howley et al.
8,067,411 B2 11/2011 Bonnert et al.
8,067,426 B2 11/2011 Biggadike et al.
8,097,718 B2 1/2012 Webber et al.
8,138,172 B2 3/2012 Cook et al.
8,143,054 B2 3/2012 Howley et al.
8,148,374 B2 4/2012 Desai et al.
8,198,082 B2 6/2012 Horiuchi et al.
8,217,069 B2 7/2012 Yonekubo et al.
8,309,098 B2 11/2012 Howley et al.
8,367,670 B2 2/2013 Desai et al.
8,476,270 B2 7/2013 Halcomb et al.
8,478,535 B2 7/2013 Jojic et al.
8,507,507 B2 8/2013 Halcomb et al.
8,513,184 B2 8/2013 Appleby et al.
8,629,142 B2 1/2014 Desai et al.
8,637,036 B2 1/2014 Mascola et al.
8,642,756 B2 2/2014 Ross et al.
8,728,465 B2 5/2014 Black et al.
8,728,486 B2 5/2014 David et al.
8,729,088 B2 5/2014 Carson et al.
8,809,527 B2 8/2014 Desai et al.
8,962,652 B2 2/2015 Halcomb et al.
8,993,755 B2 3/2015 Graupe et al.
9,017,691 B2 4/2015 Barouch et al.
9,127,006 B2 9/2015 Desai et al.
9,133,478 B2 9/2015 Moss et al.
9,133,480 B2 9/2015 Moss et al.
9,161,934 B2 10/2015 Halcomb et al.
9,452,154 B2 9/2016 Delaney, IV et al.
9,452,166 B2 9/2016 Desai et al.
9,573,952 B2 2/2017 Allen et al.
9,611,268 B2 4/2017 Graupe et al.
9,738,646 B2 8/2017 Brown et al.
9,988,425 B2 * 6/2018 Brander ............... C07K 14/005
10,172,860 B2 1/2019 Desai et al.
10,202,384 B2 2/2019 Brown et al.
10,508,117 B2 12/2019 Andres et al.
10,815,278 B2 10/2020 Brander et al.
11,072,615 B2 7/2021 Brown et al.
11,110,091 B2 9/2021 Desai et al.
11,116,774 B2 * 9/2021 Geleziunas .......... A61K 31/675
2002/0151678 A1 10/2002 Arlinghaus
2002/0173655 A1 11/2002 Dellaria et al.
2003/0044428 A1 3/2003 Moss et al.
2003/0065005 A1 4/2003 Charles et al.
2003/0100764 A1 5/2003 Bonk et al.
2003/0108562 A1 6/2003 Hanke et al.
2003/0138409 A1 7/2003 Pancre et al.
2003/0162806 A1 8/2003 Dellaria et al.
2003/0176458 A1 9/2003 Dellaria et al.
2003/0186949 A1 10/2003 Dellaria et al.
2003/0195209 A1 10/2003 Dellaria et al.
2004/0029885 A1 2/2004 Bauer et al.
2004/0073008 A1 4/2004 Iglesias et al.
2004/0105871 A1 6/2004 Robinson et al.
2004/0106136 A1 6/2004 Dong
2004/0116362 A1 6/2004 Sartorelli et al.
2004/0132748 A1 7/2004 Isobe et al.
2004/0223977 A1 11/2004 Diamond
2005/0043239 A1 2/2005 Douangpanya et al.
2005/0249742 A1 11/2005 Ruprecht et al.
2006/0052403 A1 3/2006 Isobe et al.
2006/0095241 A1 5/2006 Jojic et al.
2006/0121810 A1 6/2006 Rodrigues
2006/0160070 A1 7/2006 Mallal et al.
2006/0190226 A1 8/2006 Jojic et al.
2006/0257865 A1 11/2006 Mallal
2006/0269936 A1 11/2006 Vlach et al.
2007/0015721 A1 1/2007 Beaton et al.
2007/0048861 A1 3/2007 Robinson et al.
2007/0190071 A1 8/2007 Kurimoto et al.
2007/0197478 A1 8/2007 Jones et al.
2007/0197558 A1 8/2007 Betebenner et al.
2007/0248584 A1 10/2007 Kent
2008/0008682 A1 1/2008 Chong et al.
2008/0167289 A1 7/2008 Kay et al.
2008/0182863 A1 7/2008 Simmen et al.
2008/0199493 A1 8/2008 Picker et al.
2008/0234255 A1 9/2008 Chen
2008/0269240 A1 10/2008 Hashimoto et al.
2008/0300244 A1 12/2008 Bonnert et al.
2008/0306244 A1 12/2008 Hanke et al.
2009/0005560 A1 1/2009 Oka et al.
2009/0047249 A1 2/2009 Graupe et al.
2009/0060947 A1 3/2009 Tartaglia et al.
2009/0082332 A1 3/2009 Abbot et al.
2009/0099216 A1 4/2009 Millichip et al.
2009/0105212 A1 4/2009 Isobe et al.
2009/0118263 A1 5/2009 Hashimoto et al.
2009/0131458 A1 5/2009 Lazarides et al.
2009/0143400 A1 6/2009 Mcinally et al.
2009/0192153 A1 7/2009 Hashimoto et al.
2009/0202484 A1 8/2009 Chong et al.
2009/0203144 A1 8/2009 Beaton et al.
2009/0209524 A1 8/2009 Bennett et al.
2009/0221551 A1 9/2009 Kshirsagar et al.
2009/0221556 A1 9/2009 Kshirsagar et al.
2009/0221631 A1 9/2009 Jones et al.
2009/0252754 A1 10/2009 Caputo et al.
2009/0263470 A1 10/2009 Coller et al.
2009/0291938 A1 11/2009 Cao et al.
2009/0324551 A1 12/2009 Carson et al.
2009/0325877 A1 12/2009 Grunt et al.
2010/0015230 A1 1/2010 Ron
2010/0029585 A1 2/2010 Howbert et al.
2010/0055119 A1 3/2010 Stoloff et al.
2010/0075995 A1 3/2010 Biggadike et al.
2010/0087443 A1 4/2010 Bonnert et al.
2010/0088037 A1 4/2010 Mallal
2010/0093998 A1 4/2010 Isobe et al.
2010/0099870 A1 4/2010 Isobe et al.
2010/0120799 A1 5/2010 Lazarides et al.
2010/0130491 A1 5/2010 Bonnert et al.
2010/0135994 A1 6/2010 Banchereau et al.
2010/0143301 A1 6/2010 Desai et al.
2010/0152230 A1 6/2010 Dellaria et al.
2010/0210598 A1 8/2010 Carson et al.
2010/0215642 A1 8/2010 Lan et al.
2010/0215695 A1 8/2010 Filinova
2010/0240623 A1 9/2010 Cook et al.
2010/0256169 A1 10/2010 Averett

(56) References Cited

U.S. PATENT DOCUMENTS

| | | | |
|---|---|---|---|
| 2010/0280001 | A1 | 11/2010 | Bonnert et al. |
| 2010/0291061 | A1 | 11/2010 | Jiang |
| 2010/0298364 | A1 | 11/2010 | Bennett et al. |
| 2010/0304483 | A1 | 12/2010 | Abulafia-lapid et al. |
| 2011/0008417 | A1 | 1/2011 | Peut et al. |
| 2011/0014221 | A1 | 1/2011 | Kang et al. |
| 2011/0028715 | A1 | 2/2011 | Isobe et al. |
| 2011/0053893 | A1 | 3/2011 | Wu et al. |
| 2011/0098248 | A1 | 4/2011 | Halcomb et al. |
| 2011/0123485 | A1 | 5/2011 | Desrosiers et al. |
| 2011/0159025 | A1 | 6/2011 | Littman et al. |
| 2011/0195083 | A1 | 8/2011 | Anglister et al. |
| 2011/0217307 | A1 | 9/2011 | Hovanessian et al. |
| 2011/0277046 | A1 | 11/2011 | Barton et al. |
| 2011/0282061 | A1 | 11/2011 | Johnson |
| 2011/0305670 | A1 | 12/2011 | Farzan |
| 2011/0305749 | A1 | 12/2011 | Duch et al. |
| 2011/0311585 | A1 | 12/2011 | Berman et al. |
| 2012/0021000 | A1 | 1/2012 | Narayan et al. |
| 2012/0035193 | A1 | 2/2012 | Biggadike et al. |
| 2012/0045472 | A1 | 2/2012 | Harrison et al. |
| 2012/0082643 | A1 | 4/2012 | Ruprecht et al. |
| 2012/0107910 | A1 | 5/2012 | Liu |
| 2012/0227120 | A1 | 9/2012 | Hitchman et al. |
| 2012/0258126 | A1 | 10/2012 | Schoeller et al. |
| 2012/0263720 | A1 | 10/2012 | Grønvold et al. |
| 2012/0308593 | A1 | 12/2012 | Tartaglia et al. |
| 2013/0018042 | A1 | 1/2013 | Howbert et al. |
| 2013/0109647 | A1 | 5/2013 | Berrey et al. |
| 2013/0136776 | A1 | 5/2013 | Cleary et al. |
| 2013/0142823 | A1 | 6/2013 | Picker et al. |
| 2013/0195904 | A1 | 8/2013 | August et al. |
| 2013/0236492 | A1 | 9/2013 | Baudner et al. |
| 2013/0243726 | A1 | 9/2013 | Ray et al. |
| 2013/0302364 | A1 | 11/2013 | Mothe et al. |
| 2014/0024664 | A1 | 1/2014 | Bazin-lee et al. |
| 2014/0045837 | A1 | 2/2014 | Kurimoto et al. |
| 2014/0134132 | A1 | 5/2014 | Fu et al. |
| 2014/0142086 | A1 | 5/2014 | Howbert et al. |
| 2014/0170221 | A1 | 6/2014 | Irvine et al. |
| 2014/0220107 | A1 | 8/2014 | Kalyanaraman et al. |
| 2014/0302080 | A1 | 10/2014 | Barouch et al. |
| 2015/0004190 | A1 | 1/2015 | Bomsel et al. |
| 2015/0050310 | A1 | 2/2015 | Brander et al. |
| 2015/0105350 | A1 | 4/2015 | Ramanathan |
| 2015/0132255 | A1 | 5/2015 | Sorensen et al. |
| 2015/0132332 | A1 | 5/2015 | Shao et al. |
| 2015/0182618 | A1 | 7/2015 | Stoloff et al. |
| 2016/0008374 | A1 | 1/2016 | Geleziunas et al. |
| 2019/0055289 | A1 | 2/2019 | Brander et al. |
| 2021/0246172 | A1 | 8/2021 | Brander et al. |
| 2022/0009928 | A1 | 1/2022 | Diaz et al. |
| 2022/0062293 | A1 | 3/2022 | Geleziunas et al. |

FOREIGN PATENT DOCUMENTS

| | | | |
|---|---|---|---|
| DE | 2220246 | A1 | 12/1972 |
| DE | 2145477 | A1 | 3/1973 |
| DE | 2438037 | A1 | 2/1975 |
| DE | 2758025 | A1 | 7/1979 |
| EP | 1035123 | A1 | 9/2000 |
| EP | 1147108 | A1 | 10/2001 |
| EP | 1312678 | A1 | 5/2003 |
| EP | 1550662 | A1 | 7/2005 |
| EP | 1506223 | B1 | 11/2005 |
| EP | 1939201 | A1 | 7/2008 |
| EP | 1773999 | B1 | 9/2009 |
| EP | 2130921 | A2 | 12/2009 |
| EP | 2132209 | A1 | 12/2009 |
| EP | 2133353 | A1 | 12/2009 |
| EP | 2138497 | A1 | 12/2009 |
| EP | 2143724 | A1 | 1/2010 |
| EP | 2292642 | A1 | 3/2011 |
| EP | 2322626 | A1 | 5/2011 |
| EP | 2358757 | A1 | 8/2011 |
| EP | 2364314 | A1 | 9/2011 |
| EP | 2397489 | A1 | 12/2011 |
| EP | 2402451 | A2 | 1/2012 |
| EP | 1789438 | B1 | 4/2015 |
| EP | 2477987 | B1 | 1/2018 |
| JP | S49001576 | A | 1/1974 |
| JP | S55111420 | A | 8/1980 |
| JP | H07330770 | A | 12/1995 |
| JP | 2886570 | B2 | 4/1999 |
| JP | H11180982 | A | 7/1999 |
| JP | 2005089334 | A | 4/2005 |
| JP | 2009007273 | A | 1/2009 |
| PT | 2364314 | E | 6/2014 |
| RU | 2238946 | C2 | 10/2004 |
| TW | 200813057 | A | 3/2008 |
| TW | I401084 | B | 7/2013 |
| WO | 9014837 | A1 | 12/1990 |
| WO | 9319785 | A1 | 10/1993 |
| WO | 9320212 | A1 | 10/1993 |
| WO | 9620013 | A1 | 7/1996 |
| WO | 9702355 | A1 | 1/1997 |
| WO | 9728816 | A1 | 8/1997 |
| WO | 9744038 | A1 | 11/1997 |
| WO | 9801448 | A1 | 1/1998 |
| WO | 9805661 | A1 | 2/1998 |
| WO | 9928321 | A1 | 6/1999 |
| WO | 9932122 | A1 | 7/1999 |
| WO | 9932477 | A1 | 7/1999 |
| WO | 0000478 | A1 | 1/2000 |
| WO | 0043394 | A1 | 7/2000 |
| WO | 0119825 | A1 | 3/2001 |
| WO | 0149821 | A2 | 7/2001 |
| WO | 0188141 | A2 | 11/2001 |
| WO | 0232943 | A2 | 4/2002 |
| WO | 0242480 | A2 | 5/2002 |
| WO | 02068654 | A2 | 9/2002 |
| WO | 02076954 | A1 | 10/2002 |
| WO | 03020722 | A1 | 3/2003 |
| WO | 03080112 | A2 | 10/2003 |
| WO | 03097845 | A1 | 11/2003 |
| WO | 2004029054 | A1 | 4/2004 |
| WO | 2004076454 | A1 | 9/2004 |
| WO | 2005016348 | A1 | 2/2005 |
| WO | 2005016349 | A1 | 2/2005 |
| WO | 2005028625 | A2 | 3/2005 |
| WO | 2005030964 | A1 | 4/2005 |
| WO | 2005067901 | A2 | 7/2005 |
| WO | 2005112935 | A1 | 12/2005 |
| WO | 2005117889 | A1 | 12/2005 |
| WO | 2005120511 | A1 | 12/2005 |
| WO | 2005123736 | A1 | 12/2005 |
| WO | 2006010106 | A2 | 1/2006 |
| WO | 2006013106 | A2 | 2/2006 |
| WO | 2006034001 | A2 | 3/2006 |
| WO | 2006089106 | A2 | 8/2006 |
| WO | 2006117670 | A1 | 11/2006 |
| WO | 2006123256 | A2 | 11/2006 |
| WO | 2007014838 | A1 | 2/2007 |
| WO | 2007024707 | A2 | 3/2007 |
| WO | 2007034817 | A1 | 3/2007 |
| WO | 2007034882 | A1 | 3/2007 |
| WO | 2007034917 | A1 | 3/2007 |
| WO | 2007049771 | A1 | 5/2007 |
| WO | 2007089334 | A2 | 8/2007 |
| WO | 2007103554 | A1 | 9/2007 |
| WO | 2007104932 | A2 | 9/2007 |
| WO | 2007108968 | A2 | 9/2007 |
| WO | 2007142755 | A2 | 12/2007 |
| WO | 2007148064 | A1 | 12/2007 |
| WO | 2008004948 | A1 | 1/2008 |
| WO | 2008005555 | A1 | 1/2008 |
| WO | 2008051493 | A2 | 5/2008 |
| WO | 2008055870 | A1 | 5/2008 |
| WO | 2008101867 | A1 | 8/2008 |
| WO | 2008113711 | A1 | 9/2008 |
| WO | 2008114008 | A1 | 9/2008 |
| WO | 2008124575 | A1 | 10/2008 |
| WO | 2008124703 | A2 | 10/2008 |
| WO | 2008129994 | A1 | 10/2008 |

(56) References Cited

FOREIGN PATENT DOCUMENTS

| | | | |
|---|---|---|---|
| WO | 2008134068 | A2 | 11/2008 |
| WO | 2008135791 | A1 | 11/2008 |
| WO | 2008142479 | A2 | 11/2008 |
| WO | 2009005687 | A1 | 1/2009 |
| WO | 2009009743 | A2 | 1/2009 |
| WO | 2009019553 | A2 | 2/2009 |
| WO | 2009022185 | A2 | 2/2009 |
| WO | 2009023269 | A2 | 2/2009 |
| WO | 2009062285 | A1 | 5/2009 |
| WO | 2009067547 | A1 | 5/2009 |
| WO | 2009079335 | A1 | 6/2009 |
| WO | 2009132135 | A1 | 10/2009 |
| WO | 2010009346 | A2 | 1/2010 |
| WO | 2010018130 | A1 | 2/2010 |
| WO | 2010018131 | A1 | 2/2010 |
| WO | 2010018132 | A1 | 2/2010 |
| WO | 2010018134 | A1 | 2/2010 |
| WO | 2010037402 | A1 | 4/2010 |
| WO | 2010059732 | A1 | 5/2010 |
| WO | 2010077613 | A1 | 7/2010 |
| WO | 2010107939 | A2 | 9/2010 |
| WO | 2010130034 | A1 | 11/2010 |
| WO | 2011031965 | A1 | 3/2011 |
| WO | 2011042180 | A1 | 4/2011 |
| WO | 2011047324 | A1 | 4/2011 |
| WO | 2011049825 | A1 | 4/2011 |
| WO | 2011117408 | A1 | 9/2011 |
| WO | 2012137072 | A1 | 10/2011 |
| WO | 2012003497 | A1 | 1/2012 |
| WO | 2012003498 | A1 | 1/2012 |
| WO | 2012018856 | A2 | 2/2012 |
| WO | 2012030904 | A2 | 3/2012 |
| WO | 2012062873 | A2 | 5/2012 |
| WO | 2012087596 | A1 | 6/2012 |
| WO | 2012116142 | A2 | 8/2012 |
| WO | 2012145728 | A1 | 10/2012 |
| WO | 2012156750 | A1 | 11/2012 |
| WO | 2012172277 | A1 | 12/2012 |
| WO | 2013059442 | A2 | 4/2013 |
| WO | 2013068438 | A1 | 5/2013 |
| WO | 2013110790 | A1 | 8/2013 |
| WO | 2013110818 | A2 | 8/2013 |
| WO | 2013159064 | A1 | 10/2013 |
| WO | 2013163427 | A1 | 10/2013 |
| WO | 2013182660 | A1 | 12/2013 |
| WO | 2014026033 | A1 | 2/2014 |
| WO | 2014039840 | A1 | 3/2014 |
| WO | 2014063059 | A1 | 4/2014 |
| WO | 2015001128 | A1 | 1/2015 |
| WO | 2015007337 | A1 | 1/2015 |
| WO | 2015048512 | A1 | 4/2015 |
| WO | 2015048770 | A2 | 4/2015 |
| WO | 2015073291 | A1 | 5/2015 |
| WO | 2016007765 | A1 | 1/2016 |
| WO | 2016044182 | A1 | 3/2016 |
| WO | 2016044183 | A1 | 3/2016 |
| WO | 2019055888 | A1 | 3/2019 |
| WO | 2020234839 | A1 | 11/2020 |

OTHER PUBLICATIONS

Borducchi, E. N., et al., Dec. 2016, Ad26/MVA therapeutic vaccination with TLR7 stimulation in SIV-infected rhesus monkeys, Nature 540(284):1-16.*

Extended European Search Report for EP12382031.8 dated Dec. 12, 2012, 8 pages.

International Search Report and Written Opinion for PCT/US2020/033959, mailed on Sep. 16, 2020, 11 pages.

International Search Report for PCT/EP2013/051596 dated Sep. 20, 2013, 11 pages.

(2018) MVA.HTI and ChAdOx1.HTI, B/ES/18/ 21, Summary Notification Information Format for the Release of Genetically Modified Organisms other than Higher Plants in Accordance with Article 11 of Directive 2001/18/EC, https://gmoinfo.jrc.ec.europa.eu/bsnifs-gmo/BES-18-21.pdf, 7 pages.

Third Party Observations for PCT/US2020/033959, mailed on Sep. 22, 2021, 3 pages.

Adler Michael, W., (May 1987) "ABC of AIDS, Range and natural history of infection", British Medical Journal, 294:1145-1147.

Altman et al. (Nov. 1993) "Formation of functional peptide complexes of class II major histocompatibility complex proteins from subunits produced in *Escherichia coli*", Proc. Natl. Acad. Sci. USA, 90(21):10330-10334.

Altman et al. (Oct. 4, 1996) "Phenotypic Analysis of Antigen-Specific T Lymphocytes", Science, 274(5284):94-96.

Altschul et al. (Oct. 5, 1990) "Basic Local Alignment Search Tool", Journal of Molecular Biology, 215(3):403-410.

Altschul et al. (Sep. 1, 1997) "Gapped BLAST and PSI-BLAST: A New Generation of Protein Database Search Programs", Nucleic Acids Research, 25(17):3389-3402.

Andre et al. (Feb. 1998) "Increased Immune Response Elicited by DNA Vaccination with a Synthetic GP120 Sequence with Optimized Codon Usage", Journal of Virology, 72(2):1497-1503.

Arnold et al. (2002) "The majority of immunogenic epitopes generate CD4+ T cells that are dependent on MHC class II-bound peptide-flanking residues", The Journal of Immunology, 169(2):739-749.

Auer Henry E. (2006) "Determining the meaning of claim terms", Nature Biotechnology, 24:41-43.

Barouch et al. (2013) "Therapeutic efficacy of potent neutralizing HIV-1-specific monoclonal antibodies in SHIV-infected rhesus monkeys", Nature, 503(7475):224-239.

Barton et al. (2013) "Prospects for Treatment of Latent HIV", Nature, 93(1):46-56.

Battistini et al. (2014) "HIV-1 Latency: An Update of Molecular Mechanisms and Therapeutic Strategies", Viruses, 6:1715-1758.

Bazhan et al. (Apr. 2010) "Rational design based synthetic polyepitope DNA vaccine for eliciting HIV-specific CD8+ T cell responses", Molecular Immunology, 47(7-8):1507-1515.

Berge et al. (Jan. 1977) "Pharmaceutical Salts", Journal of Pharmaceutical Sciences, 66(1):1-19.

Betts et al. (Oct. 2003) "Sensitive and viable identification of antigen-specific CD8+ T cells by a flow cytometric assay for degranulation", Journal of Immunological Methods, 281(1-2):65-78.

Boggiano et al. (May 2005) "Discovery and characterization of highly immunogenic and broadly recognized mimics of the HIV-1 CTL epitope Gag77-85", European Journal of Immunology, 35(5):1428-1437.

Borducchi et al. (2016) "Ad26/MVA Therapeutic Vaccination with TLR7 Stimulation in SIV-Infected Rhesus Monkeys", Nature volume, 540(7632):284-287.

Borducchi et al. (Oct. 3, 2018) "Antibody and TLR7 Agonist Delay Viral Rebound in SHIV-Infected Monkeys", Nature, 564:21 pages.

Boyer et al. (2000) "Pathogenesis, diagnosis and management of hepatitis C", Journal of Hepatology, 32:98-112.

Brander et al. (Aug. 2006) "The challenges of host and viral diversity in HIV vaccine design", Current Opinion in Immunology, 18(4):430-437.

Brennan et al. (2006) "NCBI GenBank ABO61580.1", 1 page.

Brockman et al. (Nov. 2007) "Escape and Compensation from Early HLA-B57-Mediated Cytotoxic T-Lymphocyte Pressure on Human Immunodeficiency Virus Type 1 Gag Alter Capsid Interactions with Cyclophilin A", Journal of Virology, 81(22):12608-12618.

Brumme et al. (Jul. 13, 2010) "Gag Protein [Human Immunodeficiency Virus 1]", GenBank Accession No. ABY78164.1, 2 pages.

Buffa et al. (2012) "Evaluation of TLR Agonists as Potential Mucosal Adjuvants for HIV gp140 and Tetanus Toxoid in Mice", PLOS ONE, 7(12):10 pages.

Buitendijk et al. (2013) "Gardiquimod: A Toll-Like Receptor-7 Agonist That Inhibits HIV Type 1 Infection of Human Macrophages and Activated T Cells", AIDS Research and Human Retroviruses, 29(6):907-918.

Burke et al. (Nov. 1994) "The Influence of Adjuvant On The Therapeutic Efficacy Of A Recombinant Genital Herpes Vaccine", The Journal of Infectious Diseases, 170(5):1110-1119.

(56) References Cited

OTHER PUBLICATIONS

Calisher et al. (1989) “Antigenic Relationships between Flaviviruses as Determined by Cross-neutralization Tests with Polyclonal Antisera”, Journal of General Virology, 70:37-43.
Chang et al. (Nov. 2013) “Immune Activation and the Role of TLRs and TLR Agonists in the Pathogenesis of HIV-1 Infection in the Humanized Mouse Model”, Journal of Infectious Diseases, 208(S2):S145-S149.
Chang et al. (2012) “TLR7/9 antagonist reduces HIV-1-induced immune activation”, Retrovirology, 9(Suppl 2.):P172.
Chang et al. (2009) “TLR-mediated immune activation in HIV”, Blood, 113(2):269-270.
Charpentier et al. (2012) “Persistent Low-Level HIV-1 RNA Between 20 And 50 Copies/Ml In Antiretroviral-Treated Patients: Associated Factors And Virological Outcome”, Journal of Antimicrobial Chemotherapy, 67:2231-2235.
Chattopadhyay et al. (Oct. 2005) “A live-cell assay to detect antigen-specific CD4+ T cells with diverse cytokine profiles”, Nature Medicine, 11(10):1113-1117.
Chen et al. (Apr. 2013) “Molecular Mechanisms of T Cell Co-stimulation and Co-inhibition”, Nature Reviews Immunology, 13(4):227-242.
Cillo et al. (2014) “Quantification of HIV-1 latency reversal in resting CD4+ T cells from patients on suppressive antiretroviral therapy”, PNAS, 111(19):7078-7083.
Claverie et al. (Oct. 1988) “T-immunogenic peptides are constituted of rare sequence patterns. Use in the identification of T epitopes in the human immunodeficiency virus gag protein”, European Journal of Immunology, 18(10):1547-1553.
Coiras et al. “HIV-1 Latency and Eradication of Long-term Viral Reservoirs”, Retrieved from: http://www.discoverymedicine.com/Mayte-Coiras/2010/030/03/hiv-1-latency-and-eradication on Mar. 13, 2014, 12 pages.
Correia et al. (2014) “Proof of principle for epitope-focused vaccine design”, Nature, 507(7491):201-206.
Davis et al. (Dec. 1994) “Direct gene transfer in skeletal muscle: plasmid DNA-based immunization against the hepatitis B virus surface antigen”, Vaccine, 12(16):1503-1509.
Davis et al. (Nov. 1993) “DNA-based immunization induces continuous secretion of hepatitis B surface antigen and high levels of circulating antibody”, Human Molecular Genetics, 2(11):1847-1851.
Denton et al. (Jul.-Sep. 2011) “Humanized Mouse Models of HIV Infection”, AIDS Reviews, 13(3):135-148.
Desai et al. (Jul. 2014) “T-Cell Epitope Prediction Methods: An Overview”, Methods in Molecular Biology, 1184:333-364.
Di Bisceglie et al. (1999) “The Unmet Challenges of Hepatitis C”, Scientific American, Oct, 80-85.
Duque et al. (Jul. 25, 2016) “Protease, Partial [Human Immunodeficiency Virus 1]”, GenBank Accession No. AAQ17444.1, 1 page.
Dustin L.B. (2007) “Flying under the Radar: The Immunobiology of Hepatitis C”, Annual Review of Immunology, 25:71-99.
Dymock et al. (2000) “Novel Approaches to the Treatment of Hepatitis C Virus Infection”, Antiviral Chemistry & Chemotherapy, 11(2):79-96.
Ebner et al. (1993) “Identification of Multiple T Cell Epitopes on Bet v I, the Major Birch Pollen Allergen, Using Specific T Cell Clones and Overlapping Peptides”, The Journal of Immunology, 150(3):1047-54.
Eriksson et al. (Feb. 2013) “Comparative Analysis of Measures of Viral Reservoirs in HIV-1 Eradication Studies”, PLOS Pathogens, e1003174, 9(2):1-17.
Feng et al. (2000) “High-Level Expression And Mutagenesis Of Recombinant Human Phosphatidylcholine Transfer Protein Using A Synthetic Gene: Evidence For A Cterminal Membrane Binding Domain”, Biochemistry, 39(50):15399-15409.
Frahm et al. (Mar. 2004) “Consistent Cytotoxic-T-Lymphocyte Targeting of Immunodominant Regions in Human Immunodeficiency Virus across Multiple Ethnicities”, Journal of Virology, 78(5):2187-2200.
Frahm et al. (2006) “Control of human immunodeficiency virus replication by cytotoxic T lymphocytes targeting subdominant epitopes”, Nature Immunology, 7(2):173-178.
Frankel et al. (1998) “HIV-1: Fifteen Proteins and an RNA”, Annual Review of Biochemistry, 67:1-25.
French et al. (Mar. 1983) “What is a Conservative Substitution?”, Journal of Molecular Evolution, 19(12):171-175.
Frentsch et al. (Oct. 2005) “Direct access to CD4+ T cells specific for defined antigens according to CD154 expression”, Nature Medicine, 11(10):1118-1114.
Friedrich et al. (Apr. 2007) “Subdominant CD8+ T-Cell Responses Are Involved in Durable Control of AIDS Virus Replication”, Journal of Virology, 81(7):3465-3476.
Gatanaga et al. (Jul. 25, 2014) “Integrase, Partial [Human Immunodeficiency Virus 1]”, GenBank Accession No. BAO17739.1, 2 pages.
Gluck et al. (Dec. 2002) “New Technology Platforms in the Development of Vaccines for the Future”, Vaccine, 20(Suppl. 5):B10-B16.
Goodchild et al. (Jul. 2009) “Primary Leukocyte Screens for Innate Immune Agonists”, Journal of Biomolecular Screening, 14(6):723-730.
Gordon et al. (2005) “Control of Hepatitis C: A Medicinal Chemistry Perspective”, Journal of Medicinal Chemistry, 48(1):1-20.
Guillory et al. (1999) “Generation of Polymorphs, Hydrates, Solvates, and Amorphous Solids”, Polymorphism in Pharmaceutical Solids, pp. 184-227.
Gunthard et al. (2001) “Residual Human Immunodeficiency Virus (HIV) Type 1 RNA and DNA in Lymph Nodes and HIV RNA in Genital Secretions and in Cerebrospinal Fluid after Suppression of Viremia for 2 Years”, The Journal of Infectious Diseases, 183:1318-1327.
Hancock (Feb. 27, 2015) “Identification of effective Subdominant Anti-Hiv-1 CD8+ T Cells within Entire Post-infection and Post-Vaccination Immune Responses”, PLOS Pathogens, e1004658, 11(2):22 pages.
Hoffman et al. (1994) “Protection against malaria by immunization with a Plasmodium yoelii circumsporozoite protein nucleic acid vaccine”, Vaccine, 12(16):1529-1533.
Honeyborne et al. (2007) “Control of Human Immunodeficiency Virus Type 1 Is Associated with HLA-B*13 and Targeting of Multiple Gag-Specific CD8+ T-Cell Epitopes”, Journal of Virology, 81:3667-3672.
Horowitz et al. (2013) “HIV-1 suppression and durable control by combining single broadly neutralizing antibodies and antiretroviral drugs in humanized mice”, PNAS USA, pp. 16538-16543.
Horsmans et al. (2005) “Isatoribine, an agonist of TLR7, reduces plasma virus concentration in chronic hepatitis C infection”, Hepatology, 42(3):724-731.
Huarte et al. (2002) “Enhancing Immunogenicity of a CTL Epitope from Carcinoembryonic Antigen by Selective Amino Acid Replacements”, Clinical Cancer Research, 8(7):2336-2344.
Hubert et al. (2000) “Natural history of serum HIV-1 RNA levels in 330 patients with a known date of infection”, AIDS, 14:123-131.
Humphreys et al. (2000) “High-level periplasmic expression in *Escherichia coli* using a eukaryotic signal peptide: importance of codon usage at the 5' end of the coding sequence”, Protein Expression and Purification, 20(2):252-264.
Jiang et al. (2015) “Targeting NF-KB Signaling with Protein Kinase C Agonists As an Emerging Strategy for Combating HIV Latency”, AIDS Research and Human Retroviruses, 31(1):4-12.
Jin et al. (Sep. 2006) “Synthesis and immunostimulatory activity of 8-substituted amino 9-benzyladenines as potent Toll-like receptor 7 agonists”, Bioorganic & Medicinal Chemistry Letters, 16(17):4559-4563.
John et al. (May 1, 2010) “vif Protein [Human Immunodeficiency Virus 1]”, GenBank Accession No. ADF87031.1, 1 page.
Johnson et al. (2011) “Update of the Drug Resistance Mutations in HIV-1”, ISA-USA Topics in Antiviral Medicine, 19(4):156-164.
Johnston et al. (1994) “Gene gun transfection of animal cells and Genetic Immunization”, Methods in Cell Biology, 43:353-365.

(56) References Cited

OTHER PUBLICATIONS

Julien et al. (2013) "Broadly Neutralizing Antibody PGT121 Allosterically Modulates CD4 Binding via Recognition of the HIV-gp120 V3 Base and Multiple Surrounding Glycans", PLOS Pathogens, 9(5):15 pages.
Kelly et al. (1989) "Synthesis and Antirhinovirus Activity of 6-(dimethylamino)-2-(trifluoromethyl)-9-(substituted benzyl)-9H-purines", Journal of Medicinal Chemistry, 32(8):1757-1763.
Kiepiela et al. (2007) "CD8+ T-cell responses to different HIV proteins have discordant associations with viral load", Nature Medicine, 13(1):46-53.
Kiepiela et al. (2004) "Dominant influence of HLA-B in mediating the potential co-evolution of HIV and HLA", Nature, 432(7018):769-775.
Korba et al. (May 2000) "Treatment of chronic woodchuck hepatitis virus infection in the Eastern woodchuck (Marmota monax) with nucleoside analogues is predictive of therapy for chronic hepatitis B virus infection in humans", Hepatology, 31(5):1165-1175.
Kusk et al. (1993) "NCBI GenBank Accession No. AAB24615", 1 page.
Kwong et al. (2012) "Human Antibodies that Neutralize HIV-1: Identification, Structures, and B Cell Ontogenies", Immunity, 37:412-425.
Lanford et al. (2013) "GS-9620, an Oral Agonist of Toll-Like Receptor-7, Induces Prolonged Suppression of Hepatitis B Virus in Chronically Infected Chimpanzees", Gastroenterology, 144:1508-1517.
Lee et al. (Mar. 2006) "Activation of anti-hepatitis C virus responses via Toll-like receptor 7", Proceedings of the National Academy of Sciences, 103(6):1828-1833.
Leslie et al. (Mar. 2004) "HIV Evolution: CTL Escape Mutation And Reversion after Transmission", Nature Medicine, 10(3):282-289.
Lewin et al. (Nov. 15, 2018) "HIV Rebound Prevented in Monkeys", Nature, 563:333-334.
Loveday (1995) "Prediction of progression to AIDS with serum HIV-1 RNA and CD4 count", The Lancet, 345:790-791.
Malbec et al., (Dec. 16, 2013) "Broadly Neutralizing Antibodies that Inhibit HIV-1 Cell to Cell Transmission", Journal of Experimental Medicine, 210(13):2813-2821.
Mamadou et al. (2005) "NCBI GenBank Accession Nos. CAD48448 and CAD48441", 6 pages.
Mannering et al. (Dec. 2003) "A sensitive method for detecting proliferation of rare autoantigen-specific human T cells", Journal of Immunological Methods, 283(1-2):173-183.
Marsden et al. (2014) "Neutralizing the HIV Reservoir", Cell, 158:971-972.
Masemola et al. (2004) "Novel and Promiscuous CTL Epitopes in Conserved Regions of Gag Targeted by Individuals with Early Subtype C HIV Type 1 Infection from Southern Africa", Journal of Immunology, 173(7):4607-4617.
Masquelier et al. (Jul. 26, 2016) "Reverse Transcriptase, Partial [Human Immunodeficiency Virus]", GenBank Accession No. CAB51523, 1 page.
Mayr et al. (1975) "Abstammung, Eigenschaften und Verwendung des attenuierten Vaccinia-Stammes MVA", Infection, 3:6-14.
Mcgettigan et al. (2003) "Functional human immunodeficiency virus type 1 (HIV-1) Gag-Pol or HIV-1 Gag-Pol and env expressed from a single rhabdovirus-based vaccine vector genome", Journal Of Virology, 77(20):10889-10899.
Menne et al. (Jan. 2007) "The woodchuck as an animal model for pathogenesis and therapy of chronic hepatitis B virus infection", World Journal of Gastroenterology, 13(1):104-124.
Meyer et al. (Jul. 2008) "Clinical Investigations of Toll-Like Receptor Agonists", Expert Opinion on Investigational Drugs, 17(7):1051-1065.
Moennig et al. (1992) "The Pestiviruses", Advances in Virus Research, 41:53-98.
Mofenson et al. (1997) "The Relationship between Serum Human Immunodeficiency Virus Type 1 (HIV-1) RNA Level, CD4 Lymphocyte Percent, and Long-Term Mortality Risk in HIV-1-Infected Children", The Journal of Infectious Diseases, 175:1029-1038.
Moody et al. (Mar. 15, 2014) "Toll-Like Receptor 7/8 (TLR7/8) and TLR9 Agonists Cooperate to Enhance HIV-1 Envelope Antibody Responses in Rhesus Macaques", Journal of Virology, 88(6):3329-3339.
Moradpour et al. (2007) "Replication of Hepatitis C Virus", Nature Reviews Microbiology, 5(6):453-463.
Morellet et al. (Mar. 2, 2007) "Chain A, Gag Polyprotein", GenBank Accession No. 1U57_A, 1 page.
Mothe et al. (2012) "A minimal T-cell immunogen designed to cover HIV-1 specificities associated with control is immunogenic in mice and breaks CTL immunodominance", Retrovirology, 9(Suppl 2):P305.
Mothe et al. (2011) "Definition of the viral targets of protective HIV-1-specific T cell responses", Journal of Translational Medicine, 9(1):208; pp. 1-20.
Narum et al. (Dec. 2021) "Codon Optimization of Gene Fragments Encoding Plasmodium falciparum Merzoite Proteins Enhances DNA Vaccine Protein Expression and Immunogenicity in Mice", Infection and Immunity, 69(12):7250-7253.
Ngumbela et al. (Aug. 2008) "Targeting of a CD8 T Cell Env Epitope Presented by HLA-B*5802 Is Associated with Markers of HIV Disease Progression and Lack of Selection Pressure", AIDS Research and Human Retroviruses, 24(1):72-82.
Nickle et al. (Mar. 7, 2003) "Consensus and Ancestral State HIV Vaccines", Science, 299(5612):1515-1518.
Novak et al. (Dec. 1999) "MHC Class II Tetramers Identify Peptide-specific Human CD4(+) T Cells Proliferating in Response to Influenza A Antigen", Journal of Clinical Investigation, 104(12):R63-R67.
Ntemgwa et al. (Jul. 26, 2016) "Reverse Transcriptase, Partial [Human Immunodeficiency Virus 1]", GenBank Accession No. ABU62725.1, 1 page.
Ondondo et al. (2016) "Novel Conserved-region T-cell Mosaic Vaccine With High Global HIV-1 Coverage is Recognized by Protective Responses in Untreated Infection", Molecular therapy, 24(4):832-842.
Ostrowski et al. (2008) "Residual Viraemia in HIV-1-infected Patients with Plasma Viral Load <or=20 copies/ml is Associated with Increased Blood Levels of Soluble Immune Activation Markers, Scandinavian", Journal of Immunology, 68:652-660.
Outchkourov et al. (Mar. 2002) "Optimization of the Expression of Equistatin in Pichia pastoris", Protein Expression and Purification, 24(1):18-24.
Persaud et al. (2000) "A Stable Latent Reservoir For HIV-1 In Resting CD4+ T Lymphocytes In Infected Children", The Journal of Clinical investigation, 105(7):995-1003.
Picker et al. (2013) "Antibodies Advance The Search For A Cure", Nature, 503:207-208.
Powell et al. (Jul. 25, 2016) "Pol Protein, Partial [Human Immunodeficiency Virus 1]", GenBank Accession No. ADF35429.1, 1 page.
Prince et al. (2014) "Common Antiviral Agents", 9 pages.
Rasmussen et al. (2013) "Eliminating the latent HIV reservoir by reactivation strategies", Human Vaccines & Immunotherapeutics, 9(4):790-799.
Robbins et al. (Oct. 2002) "Molecular Analysis in Support of an Investigation of a Cluster of HIV-1-Infected Women", AIDS Research and Human Retroviruses, 18(15):1157-1161.
Robinson et al. (1993) "Protection Against a Lethal Influenza Virus Challenge by Immunization with a Haemagglutinin-expressing Plasmid DNA", Vaccine, 11(9):957-960.
Roethle et al. (2013) "Identification and Optimization of Pteridinone Toll-like Receptor 7 (TLR7) Agonists for the Oral Treatment of Viral Hepatitis", Journal of Medicinal Chemistry, 56(18):7324-7333.
Rosati et al. (Sep. 15, 2009) "DNA Vaccination In Rhesus Macaques Induces Potent Immune Responses And Decreases Acute And Chronic Viremia After Sivmac251 Challenge", PNAS, USA, 106(37):15831-15836.

(56) References Cited

OTHER PUBLICATIONS

Salvat et al. (2014) "Computationally Driven Deletion Of Broadly Distributed T Cell Epitopes In A Biotherapeutic Candidate", Cellular and Molecular Life Sciences, 71(24):4869-4880.
Saurya S. (Apr. 15, 2005) "nef Protein [Human immunodeficiency virus 1]", GenBank Accession No. CAD23386.1, 1 page.
Schlaepfer et al. (March 1, 200) "TLR7/8 Triggering Exerts Opposing Effects in Acute versus Latent HIV Infection", The Journal of Immunology, 176(5):2888-2895.
Schneidewind et al. (Nov. 2007) "Escape from the Dominant HLA-B27-Restricted Cytotoxic T-Lymphocyte Response in Gag Is Associated with a Dramatic Reduction in Human Immunodeficiency Virus Type 1 Replication", Journal of Virology, 81(22):12382-12393.
Schwartz et al. (Dec. 1992) "Mutational Inactivation Of An Inhibitory Sequence In Human Immunodeficiency Virus Type 1 Results In Rev-Independent Gag Expression", Journal of Virology, 66(12):7176-7182.
Scott et al. (2002) "Interferon-a-2b Plus Ribavirin: A Review of its Use in the Management of Chronic Hepatitis C", Drugs, 62(3):507-556.
Sette et al. (Sep.-Dec. 2001) "The Development of Multi-epitope Vaccines: Epitope Identification, Vaccine Design and Clinical Evaluation", Biologicals, 29(3-4):271-276.
Shafer et al. (2008) "HIV-1 Drug Resistance Mutations: An Updated Framework for the Second Decade of HAART", AIDS Reviews, 10(2):67-84.
Shafer R (Jan. 2012) "Assay For Antiretroviral Resistance", HIV insite knowledge base chapter (http://hivinsite.ucsf.edu/InSite?page=kb-02-02-03).
Shang et al. (Aug. 2009) "Rational Optimization Of Tumor Epitopes Using In Silico Analysis-Assisted Substitution Of TCR Contact Residues", European Journal of Immunology, 39(8):2248-2258.
Shingai et al. (2013) "Antibody-Mediated Immunotherapy Of Macaques Chronically Infected With SHIV Suooresses Viraemia", Nature, 503:277-291.
Siliciano et al. (2011) "HIV Latency", Cold Spring Harbor Perspectives in Medicine, 20 pages.
Smith et al. (2014) "Developments In HIV-1 Immunotherapy And Therapeutic Vaccination", F1000Prime Reports, 6:43.
Sun et al. (Jan. 2009) "Functional Characterization Of Ex Vivo Blood Myeloid And Plasmacytoid Dendritic Cells After Infection With Dengue Virus", Virology, 383(2):207-215.
Tennant et al. (1999) "Animal Models Of Hepatitis B Virus Infection", Clinics in Liver Disease, 32):241-266.
Terpe K, (2003) "Overview Of Tag Protein Fusions: From Molecular And Biochemical Fundamentals To Commercial Systems", Applied Microbiology and Biotechnology, 60(5):523-533.
Thomas et al. (2007) "Investigating Toll-Like Receptor Agonists For Potential To Treat Hepatitis C Virus Infection", Antimicrobial Agents and Chemotherapy, 51(8):2969-2978.
Tigges et al. (May 15, 1996) "Human Herpes Simplex Virus (HSV)-Specific CD8+ CTL Clones Recognize HSV-2-Infected Fibroblasts After Treatment With IFN-Gamma Or When Virion Host Shutoff Functions Are Disabled", The Journal of Immunology, 156(10):3901-3910.
Tsai et al. (2017) "Toll-Like Receptor 7 Agonist GS-9620 Induces HIV Expression and HIV-Specific Immunity in Cells from HIV-Infected Individuals on Suppressive Antiretroviral Therapy", Journal of Virology, 91(8):e02166-16(20 pages).
Tseng et al. (Jul. 2, 2013) "Anti-CD47 Antibody—Mediated Phagocytosis of Cancer by Macrophages Primes an Effective Antitumor T-Cell Response", Proceedings of the National Academy of Sciences of the United States of America, 110(27):11103-11108.
Van Der Sluis et al. (2013) "Dendritic Cell-induced Activation of Latent HIV-1 Provirus in Actively Proliferatino Primary T Lymphocytes", PLOS Pathooens, 9(3):15 pages.
Walker et al. (2011) "Broad Neutralization Coverage Of HIV By Multiple Highly Potent Antibodies", Nature, 477:466-471.
Watanabe et al. (Jul. 1994) "Liposome-Mediated DNA Transfer Into Chicken Primordial Germ Cells In Vivo", Molecular Reproduction and Development, 38(3):268-274.
Webster et al. (Dec. 1994) "Protection Of Ferrets Against Influenza Challenge With A DNA Vaccine To The Haemagglutinin", Vaccine, 12(16):1495-1498.
Whitney et al. (2014) "Rapid Seeding Of The Viral Reservoir Prior To SIV Viraemia In Rhesus Monkeys", Nature, 512:74-77.
Wong J. K (Sep. 15, 1996) "Reverse Transcriptase, Partial [Human Immunodeficiency Virus 1]", GenBank Accession No. AAB08224. 1, 1 page.
Xiang et al. (Feb. 1994) "Vaccination with a Plasmid Vector Carrying the Rabies Virus Glycoprotein Gene Induces Protective Immunity against Rabies Virus", Virology, 199(1):132-140.
Yerly et al. (Mar. 2008) "Increased cytotoxic T-lymphocyte Epitope Variant Cross-recognition and Functional Avidity are Associated with Hepatitis C Virus Clearance ", Journal of Virology, 82(6):3147-3153.
Zhang et al. (Jul. 24, 2016) "Gag Protein, Partial [Human Immunodeficiency Virus 1]", GenBank Accession No. AAB83205.1, 1 page.
Zhang et al. (Oct. 18, 2016) "Structural analysis reveals that Toll-like Receptor 7 is a dual receptor for Guanosine and single-stranded RNA", Immunity, 45:737-748.
Zhang et al. (Dec. 18, 2016) "Structural analysis of Toll-like Receptor 7 reveal detailed RNA sequence specificity and recognition mechanism of agonistic ligands", Cell Reports, 25:3371-3381.
Zuniga et al. (Mar. 2006) "Relative Dominance of Gag p24-Specific Cytotoxic T Lymphocytes Is Associated with Human Immunodeficiency Virus Control", Journal Of Virology, 80(6):3122-3125.
EU Clinical Trials Register: EudraCT No. 2018-002125-30. A study to evaluate how safe MVA.HTI and ChAdOx1.HTI vaccines with 11020672660, p. 6 of 7, B1000154.654 vesatolimod are in participants with early treated HIV-1 infection. Nov. 16, 2018. https://www.clinicaltrialsregister.eu/ctrsearch/trial/2018-002125-30/ES#A.
Ashizawa et al. (Sep. 20, 2002) "Iyakuhin no Takeigensho to Shoseki no Kagaku [Science of crystallization and polymorph phenomenon of pharmaceutical product]", Maruzen Planet Co. Ltd. 305-317.
Barr et al. (1998) "ISCOMSs and other saponin based adjuvants", Advanced Drug Delivery Reviews, 32:247-271.
Boyle et al. (1991) "Synthesis of a 2,4-Diaminodihydrohomopteridine, 6-Acetyl-2,4-Diamino-7,8-dihydro-9H-Pyrimido[4,5-b][1,4]Diazepine, Using a Furazano[3,4-d]Pyrimidine Precursor", Tetrahedron, 28:5259-5268.
Breault et al. (Dec. 1, 2008) "Exploring 8-Benzyl Pteridine-6,7-Diones as Inhibitors of Glutamate Racemase (MurI) in Gram-Positive Bacteria", Bioorganic & Medicinal Chemistry Letters, 18(23):6100-6103.
Brittain Hg (1999) "Polymorphism in Pharmaceutical Solids", Drugs and the Pharmaceutical Sciences, 25 pages.
Dzierba et al. (2007) "Dihydropyridopyrazinones and Dihydripterdinones as Corticotropin-Releasing Factor—a receptor antagonists: Structure—Activity Relationships and Computational Modeling", Journal of Medicinal Chemistry, 50:2269-2272.
Onodera Risako (2014) "Farumashia", 50(6):575.
Gibson et al. (2009) Pharmaceutical Preformulation and Formulation, 334-335.
Illan-Cabeza et al. (Jun. 18, 2018) "Anti proliferative effects of palladium( II) complexes of 5-nitrosopyrimidines and interactions with the proteolytic regulatory enzymes of the renin-angiotensin system in tumoral brain cells", Journal of Inorganic Biochemistry, 126:118-127.
Isobe et al. (2006) "Synthesis and biological evaluation of novel-9-substituted-8-hydroxyadenine derivatives as potent interferon inducers", Journal of Medicinal Chemistry, 49(6):2088-2095.
Juricova et al. (1995) "Synthesis of Base-Modified 'Abbreviated' NAO Analogues", Collection of Czechoslovak Chemical Communications, 60(2):237-250.
Matsuoka et al. (Oct. 22, 2010) "Kesshotake no Kiso to Oyo [Fundamentals and application of crystalline polymorphs]", CMC Publishing Co. Ltd. 22 pages.

(56) References Cited

OTHER PUBLICATIONS

Moye C.J. (Dec. 31, 1964) "The Synthesis of 4,6-dihydroxy-2-methoxy pyrimidine and derived pyrimidine intermediates", Australian Journal of Chemistry, 17(11):1309-1310.
Nagashima et al. (2004) "Solution-phase parallel synthesis of an N-alkylated dihydropteridinone library from fluorous amino acids", ACS Combinatorial Science, 6(6):942-949.
Stahly et al. (2007) "Diversity in Single-and Multiple-Component Crystals. The Search for and Prevalence of Polymorphs and Cocrystals, Crystal Growth & Design", SSCI, West Lafayette, Indiana. 7:1007-1026.
Susvilo et al. (Mar. 13, 2006) "Study on the reaction of methyl N-Methyl-N-(6-substituted-5-nitropyrimidin-4-yl)glycinates with sodium alkoxides", Journal of Heterocyclic Chemistry, 43(2):267-276.
Office Action in China Patent Application No. 201310465647.7 with English Translation, mailed on Mach 12, 2015.
Office Action in China Patent Application No. 201310465647.7 with English Translation, mailed on Oct. 30, 2014.
Office Action in Colombia Patent Application No. 11067510 with English translation mailed on 2012.
Office Action in Eurasian Patent Application No. EA201190021, with English Translation mailed on dated Mar. 2013.
Office Action in Eurasian Patent Application No. EA201190021, with English Translation mailed on dated Nov. 2013.
Examination Report for European Patent Application No. EP107608317, mailed on Oct. 12, 2015, 4 pages.
International Preliminary Report on Patentability and Written Opinion for PCT International Application No. PCT/US2009/041432, mailed on Oct. 26, 2010, 7 pages.
International Preliminary Report on Patentability and Written Opinion for PCT International Application No. PCT/US2010/049471, mailed on Mar. 27, 2012, 7 pages.
International Preliminary Report on Patentability and Written Opinion for PCT International Application No. PCT/US2015/057932, mailed on Apr. 15, 2016, 17 pages.
International Preliminary Report on Patentability and Written Opinion for PCT International Application No. PCT/US2015/057933, mailed on Jan. 21, 2016, 9 pages.
International Preliminary Report on Patentability and Written Opinion for PCT International Application No. PCT/US2015/057934, mailed on Mar. 18, 2016, 20 pages.
International Search Report and Written Opinion for PCT International Application No. PCT/US2015/050037, mailed on Dec. 3, 2015, 10 pages.
International Search Report and Written Opinion for PCT International Application No. PCT/US2016/052092, mailed on Nov. 10, 2016, 11 pages.
International Search Report and Written Opinion for PCT International Application No. PCT/US2017/028251, mailed on Nov. 16, 2017, 22 pages.
International Search Report and Written Opinion for PCT International Application No. PCT/US2018/029974, mailed on Sep. 18, 2018, 21 pages.
International Search Report and Written Opinion for PCT/US2015/039776, mailed on Sep. 16, 2015, 7 pages.
International Search Report and Written Opinion for PCT/US2015/050039, mailed on Feb. 24, 2016, 16 pages.
Extended European Search Report received in EP Application No. 14158708.9, mailed on Dec. 1, 2014.
Japanese Office Action issued in Japanese Application No. JP2011540807, with English Translation mailed on dated Jan. 6, 2014.
Japanese Office Action issued in Japanese Application No. JP2014139372, with English Translation mailed on dated Oct. 28, 2015.
Office Action received in Pakistan Patent Application No. 451/2015, mailed on dated Aug. 2, 2016, 5 pages.
Office Action received in Taiwan Patent application No. TW104102090, with English Translation mailed on dated Sep. 9, 2015.
Office Action received in Taiwan Patent application No. TW98141711, with English Translation mailed on 2013.
Office Action received in Ukraine Patent No. UA201108585, with English Translation mailed on 2014.
Office Action received in Vietnam Application No. VN1201101604 with English Translation mailed on dated Sep. 30, 2013.
Lim et al. (May 2, 2018) "TLR7 Agonists Induce Transient Viremia and Reduce the Viral Reservoir in SIV-infected Rhesus Macaques on Antiretroviral Therapy", Science Translational Medicine, 10(439):eaao4521(26 pages).
Sun et al., "Research Progress of AIDS Vaccines" Chin J. AIDS STD 25(4)421-424, Apr. 2019, (English Abstract).
Stevceva, "Toll-Like Receptor Agonists as Adjuvants for HIV Vaccines" Current Medicinal Chemistry 18(33):5079-5082, Nov. 1, 2011.
EP Application No. 22188059.4 Examination Report dated Jan. 17, 2025.

* cited by examiner

METHOD OF INDUCING AN HIV-1-SPECIFIC IMMUNE RESPONSE USING A CHIMPANZEE ADENOVIRUS VECTOR ENCODING AN HIVACAT T-CELL IMMUNOGEN AND TLR7 AGONIST

CROSS-REFERENCES TO RELATED APPLICATIONS

This application claims priority to U.S. Provisional Application No. 62/851,363, filed May 22, 2019, which is incorporated herein in its entirety for all purposes.

SEQUENCE LISTING

This application contains a Sequence Listing which has been submitted electronically in ASCII format and is hereby incorporated by reference in its entirety. Said ASCII copy, created on Apr. 29, 2020, is named 1300PF_ST25.txt and is 14,473 bytes in size.

BACKGROUND

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*. TLRs are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR7 recognizes and responds to imiquimod, and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines. Agonists of TLR7 are immunostimulants and can induce the production of endogenous interferon-α in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections.

TLR7 modulating compounds include the TLR7 agonist compounds of U.S. Pat. Nos. 8,367,670; 8,629,142; and 8,809,527, demonstrated through IFN-α Minimum Effective Concentration (MEC). The activity of TLR7 agonist GS-9620 has been discussed in the articles of Lanford et al., *Gastroenterology* 2013, 144(7), 1508-17, and Roethle, P. et al., *J. Med. Chem.* 2013, 56(18), 7324-7333, which discussed the TLR7 agonist activity of compounds of in U.S. Pat. Nos. 8,367,670; 8,629,142; and 8,809,527, including those of Examples 4, 49, 89, 99, and 105.

Around the world more than 36 million people are infected by the HIV virus. Numerous drugs and combination therapies have been developed for the treatment of HIV infections in humans. While combination antiretroviral therapies (cART) and highly active antiretroviral therapies (HAART) have been able to reduce HIV viral activation, often below 50 copies of HIV RNA/ml of plasma, no therapy has provided elimination of HIV infected cells which are not actively replicating HIV, commonly referred to as a patient's latent reservoir of HIV. Strategies have been sought for "kick and kill" methods of treating HIV in which the cells of the latent reservoir are to "kick" the HIV-infected cells into inducing transcription of the quiescent, replication-competent HIV proviruses, creating a state of transient viremia and making the activated cells susceptible to the "kill" from antiretroviral therapies. "Kick" programs have tested various agents, including histone deacetylase inhibitors, disulfiram, PD-1 antibodies, and HIV vaccines, as noted in Barton, K. M. et al., *Clin. Pharmacol. Ther.* 2013, 93(1), 46-56; Marsden, M. D. et al., *Cell* 2014, 158(5), 971-972; Battistini, A. et al., *Viruses* 2014, 6(4), 1715-1758; and Cillo, A. R. et al., *Proc. Natl. Acad. Sci.* 2014, 111(19), 7078-7083.

Increased access to highly active combination antiretroviral therapy (cART) has resulted in a dramatic decrease in morbidity and mortality associated with infection by the human immunodeficiency virus (HIV). However, despite having new classes of antiretroviral drugs, currently available cART regimens are not able to eradicate HIV from the body. Consequently, cART cessation in participants maintaining undetectable viral load is followed by a rebound in viremia. This reflects the inability of the standard cART in eliminating a viral reservoir formed by latently infected cells in which the integrated provirus remains quiescent and stable from early stages of infection, and the inability of the immune response effectively to contain viral rebound after treatment interruption.

Even though cART results in control of the viral load (thus preventing the development of AIDS and virus transmission), it has several issues:

(a) Not curative: cART are treatments for life. If a person stops the treatment, the viral load rebounds to initial levels generally within 2-4 weeks, making this person infective again.

(b) Adherence issues: 30 to 50% of patients are not able to control the viral load, because the treatment regime is not rigorously followed. This has much to do with psychological stress—living with HIV with no cure in sight affects a patient's quality of life—and even without that, patients are inconvenienced by their treatment routines to varying degrees (aka "pill fatigue").

(c) Resistance: HIV can develop resistance to cART.

(d) Side-effects: because of the long-term toxicity of cART, patients may suffer from cardiovascular diseases, dyslipidaemias, hypertension, diabetes, osteoporosis, or kidney diseases.

(e) High cost: treating a patient with cART costs about $20,000 per year, while the total cost for the health system during the patient lifetime is calculated to be over $400,000.

(f) Social stigma: the stigma surrounding HIV makes people reluctant to get tested, or to disclose their HIV status; it also limits their access to available HIV treatment.

There remains a need for new agents and therapies capable of assisting in the activation of the latent HIV-infected cells to enhance the activity of antiretroviral therapies and immune responses.

BRIEF SUMMARY

In one embodiment, the present disclosure provides a method of treating or preventing an HIV infection in a human in need thereof suffering from HIV infection or at risk of developing HIV infection, the method comprising administering to the human a therapeutically effective amount of a compound of Formula (I):

(I)

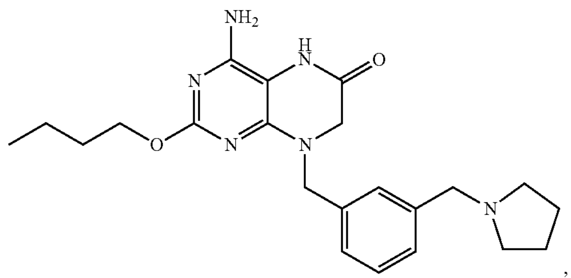

, or a pharmaceutically acceptable salt thereof, and a first virus comprising a nucleic acid encoding an immunogenic polypeptide comprising:

(i) a sequence having at least 90% sequence identity to SEQ ID NO: 1;

(ii) a sequence having at least 90% sequence identity to SEQ ID NO: 2;

(iii) a sequence having at least 90% sequence identity to SEQ ID NO: 3;

(iv) a sequence having at least 90% sequence identity to SEQ ID NO: 4;

(v) a sequence having at least 90% sequence identity to SEQ ID NO: 5;

(vi) a sequence having at least 90% sequence identity to SEQ ID NO: 6;

(vii) a sequence having at least 90% sequence identity to SEQ ID NO: 7;

(viii) a sequence having at least 90% sequence identity to SEQ ID NO: 8;

(ix) a sequence having at least 90% sequence identity to SEQ ID NO: 9;

(x) a sequence having at least 90% sequence identity to SEQ ID NO: 10;

(xi) a sequence having at least 90% sequence identity to SEQ ID NO: 11;

(xii) a sequence having at least 90% sequence identity to SEQ ID NO: 12;

(xiii) a sequence having at least 90% sequence identity to SEQ ID NO: 13;

(xiv) a sequence having at least 90% sequence identity to SEQ ID NO: 14;

(xv) a sequence having at least 90% sequence identity to SEQ ID NO: 15; and (xvi) a sequence having at least 90% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85 amino acids in length.

A method comprising administering to a human a TLR7 modulating compound and an HIV vaccine as described herein is further provided.

DETAILED DESCRIPTION

I. General

The present disclosure provides methods, compositions, and kits for the treatment or prevention of an HIV infection in a human, comprising the combination of a TLR7 modulating compound and an HIV vaccine.

II. Definitions

A "compound of the present disclosure" includes compounds disclosed herein, for example a compound of the present disclosure includes a compound of Formula (I) and pharmaceutically acceptable salts thereof.

"Tris" or tris(hydroxymethyl)aminomethane, or known during medical use as tromethamine or THAM, is a compound with the formula $(HOCH_2)_3CNH_2$.

"Modulation", "modulating" and "modulator" refer to the actions of an agent to agonize (activate or enhance) or antagonize (inhibit or diminish) the function of a biological target. Agonists or enhancers include those modulators which increase the activity of TLR7 receptors. Within each method, combination, kit, use, composition, and regimen described herein utilizing or containing a TLR7 modulator or TLR7 modulating compound there is a separate embodiment in which the TLR7 modulator or TLR7 modulating compound is an agonist of TLR7. TLR7 agonism may be determined by the PBMC assay protocol in U.S. Pat. No. 8,367,670, the contents of which are incorporated herein by reference, as well as in Bioorg. Med. Chem. Lett. 16, 4559 (2006).

"Pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

"Pharmaceutically acceptable salt" as used herein is intended to mean a salt of a compound of the present disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes without limitation pharmaceutically acceptable acid addition salts and pharmaceutically acceptable base addition salts. Lists of suitable salts are found, for example, in Berge, S. M. et al., *J. Pharm. Sci.,* 1977, 66, 1-19.

The functional equivalent or fragment of the functional equivalent, in the context of a protein, may have one or more conservative amino acid substitutions. The term "conservative amino acid substitution" refers to substitution of an amino acid for another amino acid that has similar properties as the original amino acid. The groups of conservative amino acids are as follows:

| Group | Name of the amino acids |
|---|---|
| Aliphatic | Gly, Ala, Val, Leu, Ile |
| Hydroxyl or Sulfhydryl/Selenium-containing | Ser, Cys, Thr, Met |
| Cyclic | Pro |
| Aromatic | Phe, Tyr, Trp |
| Basic | His, Lys, Arg |
| Acidic and their Amide | Asp, Glu, Asn, Gln |

Conservative substitutions may be introduced in any position of a predetermined peptide or fragment thereof. It may however also be desirable to introduce non-conservative substitutions, particularly, but not limited to, a non-conservative substitution in any one or more positions. A non-conservative substitution leading to the formation of a functionally equivalent fragment of the peptide would for example differ substantially in polarity, in electric charge, and/or in steric bulk while maintaining the functionality of the derivative or variant fragment.

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. In some cases, the percentage can be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Identical" or percent "identity" in the context of two or more nucleic acid or polypeptide sequences, refer to two or more sequences or subsequences that are the same or have a specified percentage of amino acid residues or nucleotides that are the same (e.g., 60%, 65%, 70%, 75%, 80%, 85%, 90%, 95%, 98%, or 99% identity over a specified region, e.g., the entire polypeptide sequences or individual domains of the polypeptides), when compared and aligned for maximum correspondence over a comparison window or designated region as measured using one of the following sequence comparison algorithms or by manual alignment and visual inspection. Such sequences are then said to be "substantially identical." This definition also refers to the complement of a test sequence.

A DNA sequence that "encodes" a particular RNA is a DNA nucleic acid sequence that can be transcribed into RNA. A DNA polynucleotide may encode an RNA (mRNA) that is translated into protein, or a DNA polynucleotide may encode an RNA that is not translated into protein (e.g., tRNA, rRNA, or a guide RNA; also referred to herein as "non-coding" RNA or "ncRNA"). A "protein coding sequence or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences.

"Vector," "expression vector," or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some embodiments, the vectors are plasmid, minicircles, yeast, or viral genomes. In some embodiments, the vector is a viral vector.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Therapeutically effective amount" or "effective amount" as used herein refers to an amount that is effective to elicit the desired biological or medical response, including the amount of an agent, e.g., a compound of Formula (I) or an HIV vaccine, that, when administered to a patient for treating a disease, is sufficient to effect such treatment for the disease. The effective amount will vary depending on the agent, the disease, and its severity and the age, weight, etc., of the patient to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered agents may optionally be lowered due to the combined action (e.g., additive or synergistic effects) of the agents.

"Delaying" as used herein refers to development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a patient before signs of the disease are detectable in the patient (e.g., administration of a therapeutic substance to a patient in the absence of detectable infectious agent (e.g., virus) in the patient). The patient may be an individual at risk of developing the disease or disorder, such as an individual who has one or more risk factors known to be associated with development or onset of the disease or disorder. Thus, in certain embodiments, the term "preventing HIV infection" refers to administering an anti-HIV therapeutic substance to a patient who does not have a detectable HIV infection. It is understood that the patient for anti-HIV preventative therapy may be an individual at risk of contracting the HIV virus. It is also understood that prevention does not require a 100% success rate. In some instances, prevention may be understood as a reduction of the risk of infection, but not a complete elimination in the occurrence of an infection.

"At risk human" as used herein refers to a person who is at risk of developing a condition to be treated. A person "at risk" may or may not have detectable disease or condition, and may or may not have displayed detectable disease prior to the treatment of methods described herein. "At risk" denotes that a person has one or more risk factors, which are measurable parameters that correlate with development of a disease or condition and are known in the art. A person having one or more of these risk factors has a higher probability of developing the disease or condition than a person without these risk factor(s).

"Viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses, e.g., HIV, is also a possible result of viral infection.

"ART" as used herein refers to anti-retroviral therapy. Generally, the term refers to combinations of anti-retroviral medications used to treat human viral infections, including HIV infections. Combinations and regimens can include multiple, often three or more, drugs such as nucleoside reverse transcriptase inhibitors (NRTIs), non-nucleoside reverse transcriptase inhibitors (NNRTIs), protease inhibitors (PIs), fusion inhibitors, CCR5 agonists, and/or integrase inhibitors.

"Viral load" and "HIV viral load" refer to the level of HIV detectable in the blood of an HIV infected human. It can be calculated by estimating the amount of virus in an involved bodily fluid. For example, it can be given in HIV RNA copies per milliliter of blood or blood plasma. An "undetectable" HIV viral load comprises a condition in which HIV RNA copies are not routinely detected by standard viral load tests, e.g., less than 50 copies HIV RNA per milliliter of blood or blood plasma.

"Viremia" refers to the measurable presence of virus or viral particles in circulation in a virally infected human. Transient viremia refers to a brief, transitory, or temporary increase in the measurable presence of virus or viral particles in circulation in a virally infected human. An example of transient HIV viremia includes a period in which the HIV-1 RNA level in the blood or plasma of an HIV infected human which has been maintained for a period of time at a concentration of less than 50 copies of HIV-1 RNA per mL briefly, transitorily, or temporarily rises to a concentration of greater than 50 copies/mL, such as from 50 to 2,000 copies/mL.

The terms "chronic set point", "set point in chronic HIV infection", "viral load set point", and "viral set point in chronic HIV infection" refer to the steady state HIV viral load established in the blood of an HIV infected human. The chronic set point can refer to a value of steady state HIV viral load after infection, following the introduction of antiretroviral therapy or treatment, including administration of ART, a TLR7 modulating compound, and/or an HIV vaccine described herein, or after cessation of antiretroviral therapy or treatment. A chronic set point can be determined in a single HIV infected human or determined as a median chronic set point in a cohort of HIV infected humans. When comparing two chronic set points, a first chronic set point can be a percentage of a second chronic set point or the second chronic set point can be a multiple of the first chronic set point. For example, a first chronic set point of 100 copies HIV-1 RNA per mL is 10% of a second chronic set point of 1000 copies HIV-1 RNA per mL, and can alternatively be described as a second chronic set point that is 10-fold higher than a first chronic set point.

A "viral rebound" refers to the observation that an undetectable HIV viral load in a virologically suppressed HIV infected human after treatment with ART often reverts to a detectable pre-therapy HIV viral load after cessation of ART. The viral rebound can occur within days or weeks, e.g., 4 weeks, after cessation of ART. A "delay in viral rebound" refers to a time period between the expected observation of viral rebound, e.g., 4 weeks, after cessation of ART as compared to the actual observed viral rebound, e.g., 12 weeks, after cessation of another therapy, e.g., administration of ART, a TLR7 modulating compound, and HIV vaccine according to the method described herein. In the above hypothetical example, the delay in viral rebound is 8 weeks after treatment of the ART, the TLR7 modulating compound, and the HIV vaccine. A delay in viral rebound can be determined in a single HIV infected human or determined as a median delay in viral rebound in a cohort of HIV infected humans.

III. Compounds

A TLR7 modulating compound that can be used in the methods, compositions, and/or kits of the disclosure is described herein. In some embodiments, the TLR7 modulating compound is a compound of Formula (I):

(I)

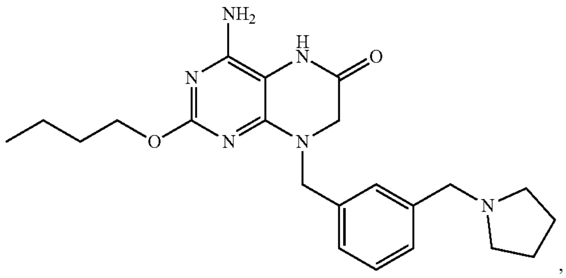

, or a pharmaceutically acceptable salt thereof.

A pharmaceutically acceptable salt of a TLR7 modulating compound described herein includes but is not limited to those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

Solid forms of the compounds of the present disclosure are also included. Crystalline forms of the TLR7 modulating compound of Formula (I) are described in U.S. Pat. Nos. 9,738,646 and 10,202,384, each of which is incorporated herein by reference in its entirety. An exemplary crystalline form of the compound of Formula (I) can be characterized by an X-ray powder diffraction (XRPD) pattern having peaks at 5.8, 11.4, 11.6, 17.7, 20.1, 20.9, 22.3, 23.9, 26.0 and 26.8 degrees 2θ (±0.2 degrees 2θ), wherein the XRPD is made using $CuK_{\alpha1}$ radiation, and a differential scanning calorimetry (DSC) plot having endotherms at about 133° C., 170° C. and 273° C. Another exemplary crystalline form of the compound of Formula (I) can be characterized by an XRPD pattern having peaks at 4.6, 9.2, 15.8, 17.8, 18.3, 19.2, 19.9, 22.4, 25.5 and 29.1 degrees 2θ (±0.2 degrees 2θ), wherein the XRPD is made using $CuK_{\alpha1}$ radiation, and DSC endotherms at about 98° C. and about 253° C.

IV. Vaccines

HIV vaccines that specifically target regions on the Gag, Pol, Vif, and Nef proteins of the HIV virus are described herein. Such HIV vaccines can induce an immunological response to one or more HIV proteins, and may either protect a human who does not have an HIV infection from contracting the virus or may have a therapeutic effect for persons infected with HIV or who later contract HIV. A vaccine generally comprises a delivery mechanism, e.g., a viral vector, and a package, such as an immunogenic composition or a nucleic acid encoding an immunogenic composition, designed to generate a desired immunological response. In some embodiments, the immunogenic composition comprises an immunogenic polypeptide that is an antigen capable of inducing an adaptive immune response, i.e., a humoral or cell-mediated immune response, when introduced in vivo.

Any viral vector capable of introducing the desired package into the body to prompt an adaptive response can be used in the presently described methods, compositions, and/or kits. In some embodiments, the viral vector comprises a live vector vaccine, an inactivated vaccine, or a modified envelope vaccine. In some embodiments, the viral vector comprises an Adenoviridae, Poxviridae, Herpesviridae, Adeno-associated virus, cytomegalovirus, carynpox, rubella poliovirus, Venezuelan equine encephalitis virus, lentivirus, or Sendai viral vector. In some embodiments, the viral vector comprises an Adenoviridae or a Poxviridae viral vector. In some embodiments, the viral vector comprises a poxvirus viral vector, e.g., a modified vaccinia virus Ankara (MVA) vector. An exemplary MVA vector is described in Barouch, D. H. et al. *Cell* 2013, 155(3), 531-539 (incorporated herein by reference in its entirety). In some embodiments, the viral vector comprises an adenovirus viral vector, such as a chimpanzee adenovirus, e.g., a replication-defective chimpanzee adenovirus. Exemplary chimpanzee adenovirus vectors have been described, e.g., in U.S. Pat. No. 9,714,435 (incorporated herein by reference in its entirety).

International Publication WO 2013/110818 and U.S. Pat. No. 9,988,425 (each of which is incorporated herein by reference in its entirety) describe immunogens for HIV vaccination. Sixteen regions in the Gag, Pol, Vif, and Nef proteins of the HIV-1 virus were relatively conserved and were targeted by HIV patients having a reduced viral load of <5000 copies of HIV-1 RNA per mL. Hancock, G. et al. *PLOS Pathogens* 2015, 11(2), e1004658; Mothe, B. et al. *J. Translational Med.* 2015, 13, 60. These regions of HIV proteins formed the basis of an immunogen for therapeutic vaccination of HIV. The following table summarizes the regions of HIV-1 targeted by the immunogens:

| HIV-1 protein | Position (HXB2) | SEQ ID NO |
|---|---|---|
| p17 | 17-94 | 1 |
| p24 | 30-43 | 2 |
| p24 | 61-71 | 3 |
| p24 | 91-150 | 4 |
| p24 | 164-177 | 5 |
| p24 | 217-231 | 6 |
| p2p7p1p6 | 63-89 | 7 |
| protease | 45-99 | 8 |
| reverse transcriptase | 34-50 | 9 |
| reverse transcriptase | 210-264 | 10 |
| reverse transcriptase | 309-342 | 11 |
| integrase | 210-243 | 12 |
| integrase | 266-282 | 13 |
| Vif | 25-50 | 14 |
| Vif | 166-184 | 15 |
| Nef | 56-68 | 16 |

The HIV numbering is as described in Korber, B. T. et al. (1998) Numbering positions in HIV relative to HXB2CG. In: Korber, C. K., Foley, B., Hahn, B., McCutchan, F., Mellors, J. and Sodroski, J (eds). *Human Retroviruses and AIDS* 1998. Theoretical Biology and Biophysics Group, Los Alamos National Laboratory, Los Alamos, N. Mex., pp. III-102-111.

In some embodiments, the HIV vaccine comprises a virus comprising an immunogenic polypeptide, or a nucleic acid encoding an immunogenic polypeptide, wherein the immunogenic polypeptide comprises:

(i) a sequence having at least 90%, 91%, 92%, 93%, 94%, 95%, 96%, 97%, 98%, or 99% sequence identity to SEQ ID NO: 1;

(ii) a sequence having at least 90%, 91%, 92%, 93%, 94%, 95%, 96%, 97%, 98%, or 99% sequence identity to SEQ ID NO: 2;

(iii) a sequence having at least 90%, 91%, 92%, 93%, 94%, 95%, 96%, 97%, 98%, or 99% sequence identity to SEQ ID NO: 3;

(iv) a sequence having at least 90%, 91%, 92%, 93%, 94%, 95%, 96%, 97%, 98%, or 99% sequence identity to SEQ ID NO: 4;

(v) a sequence having at least 90%, 91%, 92%, 93%, 94%, 95%, 96%, 97%, 98%, or 99% sequence identity to SEQ ID NO: 5;

(vi) a sequence having at least 90%, 91%, 92%, 93%, 94%, 95%, 96%, 97%, 98%, or 99% sequence identity to SEQ ID NO: 6;

(vii) a sequence having at least 90%, 91%, 92%, 93%, 94%, 95%, 96%, 97%, 98%, or 99% sequence identity to SEQ ID NO: 7;

(viii) a sequence having at least 90%, 91%, 92%, 93%, 94%, 95%, 96%, 97%, 98%, or 99% sequence identity to SEQ ID NO: 8;

(ix) a sequence having at least 90%, 91%, 92%, 93%, 94%, 95%, 96%, 97%, 98%, or 99% sequence identity to SEQ ID NO: 9;

(x) a sequence having at least 90%, 91%, 92%, 93%, 94%, 95%, 96%, 97%, 98%, or 99% sequence identity to SEQ ID NO: 10;

(xi) a sequence having at least 90%, 91%, 92%, 93%, 94%, 95%, 96%, 97%, 98%, or 99% sequence identity to SEQ ID NO: 11;

(xii) a sequence having at least 90%, 91%, 92%, 93%, 94%, 95%, 96%, 97%, 98%, or 99% sequence identity to SEQ ID NO: 12;

(xiii) a sequence having at least 90%, 91%, 92%, 93%, 94%, 95%, 96%, 97%, 98%, or 99% sequence identity to SEQ ID NO: 13;

(xiv) a sequence having at least 90%, 91%, 92%, 93%, 94%, 95%, 96%, 97%, 98%, or 99% sequence identity to SEQ ID NO: 14;

(xv) a sequence having at least 90%, 91%, 92%, 93%, 94%, 95%, 96%, 97%, 98%, or 99% sequence identity to SEQ ID NO: 15; and (xvi) a sequence having at least 90%, 91%, 92%, 93%, 94%, 95%, 96%, 97%, 98%, or 99% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85, e.g., from 11 to 82, from 11 to 80, or from 11 to 78, amino acids in length. In some embodiments, the immunogenic polypeptide comprises a sequence having amino acid sequences with no more than 1, 2, or 3 substitutions in any one of SEQ ID NOS: 1-16. In some embodiments, the immunogenic polypeptide comprises a sequence having amino acid sequences according to SEQ ID NOS: 1-16.

In some embodiments, the immunogenic polypeptide comprises an amino acid sequence having at least 90%, 91%, 92%, 93%, 94%, 95%, 96%, 97%, 98%, or 99% sequence identity to SEQ ID NO: 17. In some embodiments, the immunogenic polypeptide comprises an amino acid sequence according to SEQ ID NO: 17.

The immunogenic polypeptide can be encoded by any suitable nucleic acid sequence. In some embodiments, the nucleic acid encoding the immunogenic polypeptide comprises a nucleic acid sequence having at least 90%, 91%, 92%, 93%, 94%, 95%, 96%, 97%, 98%, or 99% sequence identity to SEQ ID NO: 18. In some embodiments, the nucleic acid encoding the immunogenic polypeptide comprises a nucleic acid sequence according to SEQ ID NO: 18.

In some embodiments, the HIV vaccine comprises a modified vaccinia virus Ankara (MVA) comprising a nucleic acid encoding an immunogenic polypeptide having an amino acid sequence according to SEQ ID NO: 17. In some embodiments, the HIV vaccine comprises a replication-defective chimpanzee adenovirus comprising a nucleic acid encoding an immunogenic polypeptide having an amino acid sequence according to SEQ ID NO: 17.

V. Compositions

In some embodiments, the present disclosure provides a pharmaceutical composition comprising a TLR7 modulating compound of Formula (I), or a pharmaceutically acceptable salt thereof, and a pharmaceutically acceptable excipient.

In some embodiments, a pharmaceutical composition comprises an HIV vaccine as described herein and a pharmaceutically acceptable excipient.

In some embodiments, the pharmaceutical composition comprises one or more additional therapeutic agents, as more fully set forth below.

Pharmaceutical compositions comprising the compound of the present disclosure, or a pharmaceutically acceptable salt thereof, may be prepared with one or more pharmaceutically acceptable excipients which may be selected in accordance with ordinary practice. Tablets may contain excipients including glidants, fillers, binders and the like. In certain embodiments, the composition comprising the TLR7 modulating compound is provided as a solid dosage form, including a solid oral dosage form.

Compositions described herein that are suitable for oral administration may be presented as discrete units (a unit dosage form) including but not limited to capsules, sachets or tablets each containing a predetermined amount of the active ingredient. In one embodiment, the pharmaceutical composition is a tablet.

Pharmaceutical compositions disclosed herein comprise one or more therapeutic agents disclosed herein, e.g., a compound of the present disclosure or an HIV vaccine, together with a pharmaceutically acceptable excipient and optionally other therapeutic agents. Pharmaceutical compositions containing the active ingredient may be in any form suitable for the intended method of administration. A pharmaceutically acceptable excipient can be any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in human.

Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment patient and the particular mode of administration. For example, in some embodiments, a dosage form of a compound of Formula (I) for oral administration to humans may contain approximately 1 to 10 mg of active material, e.g., about 2, 3, 4, 5, 6, 7, or about 8 mg, formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

Aqueous compositions, such as those used to prepare HIV vaccine formulations, may be prepared in sterile form, and when intended for delivery by other than oral administration generally may be isotonic. All compositions may optionally contain excipients such as those set forth in the Rowe et al, Handbook of Pharmaceutical Excipients, 6th edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

The amount of the virus within the HIV vaccine formulation can be measured by any means known in the art. The amount may be determined by bulk measurement of the number of viral particles (vp) within an amount of aqueous composition, e.g., by flow cytometry. Alternatively, the amount may be determined by the activity of the virus within the composition, e.g., by plaque assay. Plaque-based assays can be used to determine virus concentration in terms of infectious dose. Viral plaque assays determine the number of plaque forming units (pfu) in a virus sample, which can be used as a measure of virus quantity. See, e.g., Kaufmann, S. H.; Kabelitz, D. (2002). *Methods in Microbiology Vol. 32: Immunology of Infection*. Academic Press. ISBN 0-12-521532-0.

The compositions include those suitable for various administration routes, including oral and intramuscular administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21St Edition, Lippincott Williams and Wilkins, Philadelphia, Pa., 2006.

In some embodiments, the composition comprises from about 2 to about 6 mg, such as about 2, 3, 4, 5, or about 6 mg, e.g., 2 mg or 4 mg, of the compound of Formula (I), lactose, microcrystalline cellulose, croscarmellose sodium, magnesium stearate, polyethylene glycol, polyvinyl alcohol, talc, and titanium dioxide.

In some embodiments, the composition comprises from about $1\times10^{10}$ to about $1\times10^{11}$, e.g., about $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or about $1\times10^{11}$ viral particles (vp) in about 0.5 mL formulation buffer of a replication-defective chimpanzee adenovirus comprising a nucleic acid encoding an immunogenic polypeptide having an amino acid sequence of SEQ ID NO: 17. In some embodiments, the formulation buffer comprises about 10 mM L-Histidine. In some embodiments, the formulation buffer comprises about 35 mM NaCl. In some embodiments, the formulation buffer comprises about 7.5% (w/v) of sucrose. In some embodiments, the formulation buffer comprises about 1 mM $MgCl_2$. In some embodiments, the formulation buffer comprises about 0.1 mM EDTA disodium. In some embodiments, the formulation buffer comprises about 0.1% (w/v) Polysorbate-80. In some embodiments, the formulation buffer comprises about 0.5% (v/v) ethanol. In some embodiments, the formulation buffer has a pH of about 6.6. In some embodiments, the composition comprises $5\times10^{10}$ viral particles (vp) in 0.5 mL formulation buffer of a replication-defective chimpanzee adenovirus comprising a nucleic acid encoding an immunogenic polypeptide having an amino acid sequence of SEQ ID NO: 17, wherein the formulation buffer comprises 10 mM L-Histidine, 35 mM NaCl, 7.5% (w/v) of sucrose, 1 mM $MgCl_2$, 0.1 mM EDTA disodium, 0.1% (w/v) Polysorbate-80, 0.5% (v/v) ethanol, and a pH of 6.6.

In some embodiments, the composition comprises from about $0.5\times10^8$ to about $5\times10^8$, e.g., about $1\times10^8$, $2\times10^8$, $3\times10^8$, $4\times10^8$, or about $5\times10^8$ plaque-forming units (pfu) in about 0.5 mL Tris buffer of a modified vaccinia virus Ankara (MVA) comprising a nucleic acid encoding an immunogenic polypeptide having an amino acid sequence of SEQ ID NO: 17. In some embodiments, the composition comprises $2\times10^8$ plaque-forming units (pfu) in 0.5 mL Tris buffer of a modified vaccinia virus Ankara (MVA) comprising a nucleic acid encoding an immunogenic polypeptide having an amino acid sequence of SEQ ID NO: 17.

VI. Methods

As will be appreciated by those skilled in the art, when treating a viral infection such as HIV, such treatment may be characterized in a variety of ways and measured by a variety of endpoints. The scope of the present disclosure is intended to encompass all such characterizations.

In some embodiments, a method of treating or preventing an HIV infection in a human in need thereof suffering from HIV infection or at risk of developing HIV infection comprises administering to the human a TLR7 modulating compound of the present disclosure (e.g., a compound of Formula (I), or a pharmaceutically acceptable salt thereof) and an HIV vaccine as described herein. In some embodiments, the method is effective to induce an immune response against one or more clades of HIV. In some embodiments, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present disclosure include, among others, detecting a decrease in viral load or antigen in a patient's serum, detection of interferon (IFN)-gamma-secreting antigen specific T cells, and detection of elevated levels of one or more liver enzymes, such as alanine transferase (ALT) and aspartate transferase (AST). In one embodiment, the detection of IFN-gamma-secreting antigen specific T cells is accomplished using an ELISPOT assay or FACS analysis. Another embodiment includes reducing the viral load associated with HIV infection, including a reduction as measured by PCR testing.

TLR7 modulating compounds are capable of inducing transient viremia from latent HIV reservoirs. See, e.g., US patent publication 20160008374 (herein incorporated by reference in its entirety). Latent HIV reservoir and latent HIV infection refer to a condition in which resting CD4+ T lymphocytes or other cells are infected with HIV but are not actively producing HIV. Inactive HIV infected cells are generally referred to as latently infected cells. Anti-retroviral therapy (ART) can reduce the level of HIV in the blood to an undetectable level, while latent reservoirs of HIV continue to survive. When a latently infected cell is reactivated, the cell begins to produce HIV (HIV replication).

The method of treating or preventing an HIV infection comprising the "kick-and-kill" combination of TLR7 modulating compound of the present disclosure and an HIV vaccine as described herein can target and remove active HIV virus as well as activate latent HIV virus in order to target and to remove HIV virus from latent reservoirs. Methods of determining the level of HIV in latent reservoirs are known in the art, and include, for example, direct measurement of the level of HIV DNA in CD4+ T cells and indirect measurement of the time of viral rebound after cessation of anti-HIV therapies. An improved control of HIV viremia by the method of treating or preventing described herein can be reflected in a delay in viral rebound compared to the viral rebound observed for standard HIV therapies.

In some embodiments, the method of treating or preventing an HIV infection in a human comprising administering to the human a TLR7 modulating compound of the present disclosure and an HIV vaccine as described herein further comprises maintaining a low viral load (e.g., less than about 200, 100, 50, or about 20 copies HIV-1 RNA per mL of blood or plasma) for a period of time, e.g., from about a week to about 9 months, after cessation of anti-HIV viral treatments, including ART, the TLR7 modulating compound, and the HIV vaccine. In some embodiments, the period of time is longer after administration of the TLR7 modulating compound and the HIV vaccine compared with administration of the TLR7 modulating compound or the HIV vaccine only. In some embodiments, the period of time is a week, two weeks, three weeks, a month, 2 months, 3 months, 4 months, 5 months, 6 months, 7 months, 8 months, 9 months, or greater.

In some embodiments, a method of treating or preventing HIV infection in a human in need thereof suffering from HIV infection or at risk of developing HIV infection comprises administering to the human a TLR7 modulating compound of Formula (I) or a pharmaceutically acceptable salt thereof and an HIV vaccine. In some embodiments, the TLR7 modulating compound is a compound of Formula (I), or a pharmaceutically acceptable salt thereof. In some embodiments, the HIV vaccine comprises a virus comprising a nucleic acid encoding an immunogenic polypeptide that comprises a sequence having amino acid sequences according to SEQ ID NOS: 1-16, e.g., an immunogenic polypeptide having a sequence of SEQ ID NO: 17.

In some embodiments, the human in need thereof suffering from HIV infection is a virologically suppressed human, i.e., a virally infected human that is maintained at or below a desired viremia level for a specified human or antiviral treatment or regimen. An example of HIV virologic suppression in an HIV-infected human may be the maintenance in the human of a measurable HIV viral load of less than 200 copies of HIV-1 RNA per mL of blood or plasma. Other examples of virologic suppression would be the maintenance in the human of a viral load of less than 100 copies/mL, less than 50 copies/ml, less than 40 copies/mL, less than 30 copies/mL, and less than 20 copies/mL.

In some embodiments, the method of treating or preventing HIV infection comprises achieving virologic suppression in the human. In some embodiments, the method of treating or preventing HIV infection comprises maintaining virologic suppression in the human.

In some embodiments, virologic suppression can be achieved through other anti-HIV therapies, such as antiretroviral therapy (ART). In some embodiments, the antiretroviral therapy comprises an HIV reverse transcriptase inhibitor (e.g., a nucleoside or non-nucleoside reverse transcriptase inhibitor), an HIV integrase inhibitor, an HIV non-catalytic site (or allosteric) integrase inhibitor, an HIV entry (fusion) inhibitor, an HIV maturation inhibitor, or a combination thereof. Exemplary anti-retroviral agents include the HIV integrase catalytic site inhibitors raltegravir (ISENTRESS®; Merck), bictegravir (Gilead), elvitegravir (Gilead), soltegravir (GSK, ViiV), cabotegravir (GSK 1265744, GSK744, GSK, ViiV), and dolutegravir; HIV nucleoside reverse transcriptase inhibitors abacavir (ZIAGEN®, GSK), didanosine (VIDEX®, BMS), tenofovir disoproxil fumarate (VIREAD®, Gilead), tenofovir alafenamide (TAF), emtricitabine (EMTRIVA®, Gilead), lamivudine (EPIVIR®, GSK/Shire), stavudine (ZERIT®, BMS), zidovudine (RETROVIR®, GSK), abacavir, elvucitabine (Achillion), tenofovir exalidex (CMX-157, Chimerix), and festinavir (Oncolys); HIV non-nucleoside reverse transcriptase inhibitors nevirapine (VIRAMUNE®, BI), efavirenz (SUSTIVA®, BMS), etravirine (INTELENCE®, J&J), rilpivirine (TMC278, R278474, J&J), fosdevirine (GSK, ViiV), doravirine (MK-1439, Merck), and lersivirine (Pfizer/ViiV); HIV protease inhibitors atazanavir (REYATAZ®, BMS), darunavir (PREZISTA®, J&J), indinavir (CRIXIVAN®, Merck), lopinavir (KALETRA®, Abbvie), nelfinavir (VIRACEPT®, Pfizer), saquinavir (INVIRASE®, Hoffmann-LaRoche), tipranavir (APTIVUS®, BI), ritonavir (NORVIR®, Abbvie), and fosamprenavir (LEXIVA®, GSK/Vertex); HIV entry inhibitors maraviroc (SELZENTRY®, Pfizer), enfuvirtide (FUZEON®, Trimeris), and fostemsavir (BMS-663068, BMS); and the HIV maturation inhibitor bevirimat (Myriad Genetics).

In some embodiments, the anti-retroviral therapy comprises one or more agents selected from the group consisting of raltegravir, elvitegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, nevirapine, efavirenz, etravirine, rilpivirine, fosdevirine, doravirine, lersivirine, atazanavir, darunavir, indinavir, lopinavir, nelfinavir, saquinavir, tipranavir, ritonavir, fosamprenavir, maraviroc, enfuvirtide, fostemsavir, bevirimat, cobicistat, and bictegravir; or a pharmaceutically acceptable salt thereof. In some embodiments, the antiretroviral therapy comprises one or more agents selected from the group consisting of raltegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, rilpivirine, fosdevirine, doravirine, lersivirine, maraviroc, enfuvirtide, fostemsavir, bevirimat, and bictegravir; or a pharmaceutically acceptable salt thereof. In some embodiments, the anti-retroviral therapy comprises three or more agents, e.g., two nucleoside reverse transcriptase inhibitors and a non-nucleoside reverse transcriptase inhibitor or an integrase inhibitor In some embodiments, the method of treating or preventing an HIV infection comprises administration of a TLR7 modulating compound of Formula (I) and an HIV vaccine after administration of ART. In some embodiments, the method of treating or preventing an HIV infection comprises administration of a TLR7 modulating compound of the present disclosure and an HIV vaccine concurrently with ART. In some embodiments, the therapeutic agents of the ART is the same before and during administration of the TLR7 modulating compound and the HIV vaccine. In some embodiments, the therapeutic agents of the ART is different before and during administration of the TLR7 modulating compound and the HIV vaccine.

HIV vaccination protocols have been developed in non-human primates that comprise two different viruses, e.g., an adenovirus priming immunization vector and a modified vaccinia virus Ankara (MVA) boost vector. See, e.g., Barouch, D. H. et al. *Cell* 2013, 155(3), 531-539. This heterologous prime-boost vaccination approach may offer a more effective HIV vaccine than one using a single viral vector. Accordingly, in some embodiments, the HIV vaccine comprises a first virus and a second virus. In some embodiments, the first virus comprises an Adenoviridae or a Poxviridae viral vector, e.g., an adenovirus viral vector, for example, a chimpanzee adenovirus such as a replication-defective chimpanzee adenovirus. In some embodiments, the second virus comprises a Poxviridae viral vector, e.g., a modified vaccinia virus Ankara (MVA).

In some embodiments, a method of treating or preventing an HIV infection in a human in need thereof suffering from HIV infection or at risk of developing HIV infection comprises administering to the human a therapeutically effective amount of a compound of Formula (I):

(I)

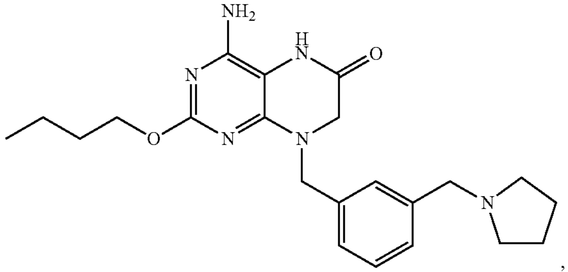

, or a pharmaceutically acceptable salt thereof, and a first virus comprising an immunogenic polypeptide, or a nucleic acid encoding an immunogenic polypeptide, wherein the immunogenic polypeptide comprises:

(i) a sequence having at least 90%, 91%, 92%, 93%, 94%, 95%, 96%, 97%, 98%, or 99% sequence identity to SEQ ID NO: 1;

(ii) a sequence having at least 90%, 91%, 92%, 93%, 94%, 95%, 96%, 97%, 98%, or 99% sequence identity to SEQ ID NO: 2;

(iii) a sequence having at least 90%, 91%, 92%, 93%, 94%, 95%, 96%, 97%, 98%, or 99% sequence identity to SEQ ID NO: 3;

(iv) a sequence having at least 90%, 91%, 92%, 93%, 94%, 95%, 96%, 97%, 98%, or 99% sequence identity to SEQ ID NO: 4;

(v) a sequence having at least 90%, 91%, 92%, 93%, 94%, 95%, 96%, 97%, 98%, or 99% sequence identity to SEQ ID NO: 5;

(vi) a sequence having at least 90%, 91%, 92%, 93%, 94%, 95%, 96%, 97%, 98%, or 99% sequence identity to SEQ ID NO: 6;

(vii) a sequence having at least 90%, 91%, 92%, 93%, 94%, 95%, 96%, 97%, 98%, or 99% sequence identity to SEQ ID NO: 7;

(viii) a sequence having at least 90%, 91%, 92%, 93%, 94%, 95%, 96%, 97%, 98%, or 99% sequence identity to SEQ ID NO: 8;

(ix) a sequence having at least 90%, 91%, 92%, 93%, 94%, 95%, 96%, 97%, 98%, or 99% sequence identity to SEQ ID NO: 9;

(x) a sequence having at least 90%, 91%, 92%, 93%, 94%, 95%, 96%, 97%, 98%, or 99% sequence identity to SEQ ID NO: 10;

(xi) a sequence having at least 90%, 91%, 92%, 93%, 94%, 95%, 96%, 97%, 98%, or 99% sequence identity to SEQ ID NO: 11;

(xii) a sequence having at least 90%, 91%, 92%, 93%, 94%, 95%, 96%, 97%, 98%, or 99% sequence identity to SEQ ID NO: 12;

(xiii) a sequence having at least 90%, 91%, 92%, 93%, 94%, 95%, 96%, 97%, 98%, or 99% sequence identity to SEQ ID NO: 13;

(xiv) a sequence having at least 90%, 91%, 92%, 93%, 94%, 95%, 96%, 97%, 98%, or 99% sequence identity to SEQ ID NO: 14;

(xv) a sequence having at least 90%, 91%, 92%, 93%, 94%, 95%, 96%, 97%, 98%, or 99% sequence identity to SEQ ID NO: 15; and (xvi) a sequence having at least 90%, 91%, 92%, 93%, 94%, 95%, 96%, 97%, 98%, or 99% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85, e.g., from 11 to 82, from 11 to 80, or from 11 to 78, amino acids in length. In some embodiments, the immunogenic polypeptide comprises a sequence having amino acid sequences with no more than 1, 2, or 3 substitutions in any one of SEQ ID NOS: 1-16. In some embodiments, the immunogenic polypeptide comprises a sequence having amino acid sequences according to SEQ ID NOS: 1-16.

In some embodiments, the method comprises the immunogenic polypeptide that comprises an amino acid sequence having at least 90%, 91%, 92%, 93%, 94%, 95%, 96%, 97%, 98%, or 99% sequence identity to SEQ ID NO: 17. In some embodiments, the immunogenic polypeptide comprises an amino acid sequence according to SEQ ID NO: 17.

In some embodiments, the method comprises the nucleic acid encoding the immunogenic polypeptide that comprises a nucleic acid sequence having at least 90%, 91%, 92%, 93%, 94%, 95%, 96%, 97%, 98%, or 99% sequence identity to SEQ ID NO: 18. In some embodiments, the nucleic acid encoding the immunogenic polypeptide comprises a nucleic acid sequence according to SEQ ID NO: 18.

In some embodiments, a method of treating or preventing an HIV infection in a human in need thereof suffering from HIV infection or at risk of developing HIV infection comprises administering to the human a therapeutically effective amount of a compound of Formula (I):

(I)

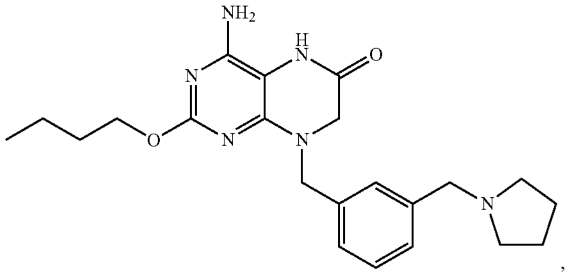

or a pharmaceutically acceptable salt thereof, and a first virus comprising a nucleic acid encoding an immunogenic polypeptide comprising:

(i) a sequence having at least 90% sequence identity to SEQ ID NO: 1;

(ii) a sequence having at least 90% sequence identity to SEQ ID NO: 2;

(iii) a sequence having at least 90% sequence identity to SEQ ID NO: 3;

(iv) a sequence having at least 90% sequence identity to SEQ ID NO: 4;

(v) a sequence having at least 90% sequence identity to SEQ ID NO: 5;

(vi) a sequence having at least 90% sequence identity to SEQ ID NO: 6;

(vii) a sequence having at least 90% sequence identity to SEQ ID NO: 7;

(viii) a sequence having at least 90% sequence identity to SEQ ID NO: 8;

(ix) a sequence having at least 90% sequence identity to SEQ ID NO: 9;

(x) a sequence having at least 90% sequence identity to SEQ ID NO: 10;

(xi) a sequence having at least 90% sequence identity to SEQ ID NO: 11;

(xii) a sequence having at least 90% sequence identity to SEQ ID NO: 12;

(xiii) a sequence having at least 90% sequence identity to SEQ ID NO: 13;

(xiv) a sequence having at least 90% sequence identity to SEQ ID NO: 14;

(xv) a sequence having at least 90% sequence identity to SEQ ID NO: 15; and (xvi) a sequence having at least 90% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85 amino acids in length.

In some embodiments of the method, the immunogenic polypeptide comprises:

(i) a sequence having at least 95% sequence identity to SEQ ID NO: 1;

(ii) a sequence having at least 95% sequence identity to SEQ ID NO: 2;

(iii) a sequence having at least 95% sequence identity to SEQ ID NO: 3;

(iv) a sequence having at least 95% sequence identity to SEQ ID NO: 4;

(v) a sequence having at least 95% sequence identity to SEQ ID NO: 5;

(vi) a sequence having at least 95% sequence identity to SEQ ID NO: 6;

(vii) a sequence having at least 95% sequence identity to SEQ ID NO: 7;

(viii) a sequence having at least 95% sequence identity to SEQ ID NO: 8;

(ix) a sequence having at least 95% sequence identity to SEQ ID NO: 9;

(x) a sequence having at least 95% sequence identity to SEQ ID NO: 10;

(xi) a sequence having at least 95% sequence identity to SEQ ID NO: 11;

(xii) a sequence having at least 95% sequence identity to SEQ ID NO: 12;

(xiii) a sequence having at least 95% sequence identity to SEQ ID NO: 13;

(xiv) a sequence having at least 95% sequence identity to SEQ ID NO: 14;

(xv) a sequence having at least 95% sequence identity to SEQ ID NO: 15; and (xvi) a sequence having at least 95% sequence identity to SEQ ID NO: 16.

In some embodiments of the method, the immunogenic polypeptide comprises the sequences of SEQ ID NOS: 1-16, wherein at least two of SEQ ID NOS: 1-16 are joined by the single, dual, or triple alanine amino acid linker, and wherein the linker results in the formation of an AAA sequence in the junction region between adjoining sequences.

In some embodiments of the method, the immunogenic polypeptide has an amino acid sequence according to SEQ ID NO: 17.

In some embodiments of the method, the nucleic acid has a nucleic acid sequence according to SEQ ID NO: 18.

In some embodiments of the method, the first virus comprises an Adenoviridae or a Poxviridae viral vector. In some embodiments, the first virus comprises an adenovirus viral vector. In some embodiments, the first virus comprises a chimpanzee adenovirus viral vector. In some embodiments, the first virus comprises a replication-defective chimpanzee adenovirus viral vector. In some embodiments, about $5\times10^{10}$ viral particles of the first virus is administered. In some embodiments, the first virus is administered once every 12 weeks. In some embodiments, the first virus is administered twice.

In some embodiments, the method further comprises administering a second virus comprising the nucleic acid encoding the immunogenic polypeptide. In some embodiments, the second virus comprises a modified vaccinia virus Ankara (MVA) vector. In some embodiments, about $2\times10^{8}$ plaque-forming units of the second virus is administered. In some embodiments, the second virus is administered once every 12 weeks. In some embodiments, the second virus is administered twice.

In some embodiments of the method, the first virus and the second virus are administered intramuscularly.

In some embodiments of the method, the first virus is administered at Week 0 and Week 12, and the second virus is administered at Week 24 and Week 36.

In some embodiments of the method, from about 6 mg to about 8 mg of the compound of Formula (I) or a pharmaceutically acceptable salt thereof is administered. In some embodiments, the compound of Formula (I) or pharmaceutically acceptable salt thereof is administered every two weeks after the third administration of virus. In some embodiments, the compound of Formula (I) is administered at Weeks 26, 28, 30, 32, 34, 38, 40, 42, 44, and 46.

In some embodiments of the method, the human is virologically suppressed. In some embodiments, the virologically suppressed human has a viral load of less than about 200, 100, 50, or about 20 copies of HIV-1 RNA per mL of plasma or blood. In some embodiments, the virological suppression results from administration of anti-retroviral therapy. In some embodiments, the anti-retroviral therapy comprises one or more agents selected from the group consisting of raltegravir, elvitegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, nevirapine, efavirenz, etravirine, rilpivirine, fosdevirine, doravirine, lersivirine, atazanavir, darunavir, indinavir, lopinavir, nelfinavir, saquinavir, tipranavir, ritonavir, fosamprenavir, maraviroc, enfuvirtide, fostemsavir, bevirimat, cobicistat, and bictegravir; or a pharmaceutically acceptable salt thereof.

In some embodiments, the method of treating or preventing HIV infection in a human in need thereof suffering from HIV infection or at risk of developing HIV infection comprises administering to the human a compound of Formula (I):

(I)

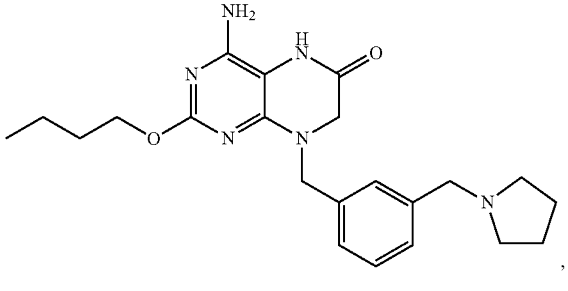

,

- a first virus comprising $5\times10^{10}$ viral particles of a replication-defective chimpanzee adenovirus comprising a nucleic acid encoding an immunogenic polypeptide having an amino acid sequence of SEQ ID NO: 17, and
- a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Week 26 and Week 28, and 6 mg of the compound of Formula (I) is administered at Weeks 30, 32, 34, 38, 40, 42, 44, and 46.

In some embodiments, the method of treating or preventing HIV infection in a human in need thereof suffering from HIV infection or at risk of developing HIV infection comprises administering to the human a compound of Formula (I):

(I)

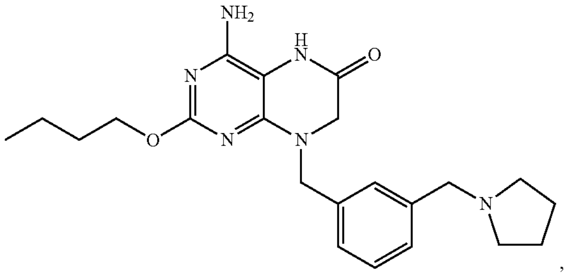

,

- a first virus comprising $5\times10^{10}$ viral particles of a replication-defective chimpanzee adenovirus comprising a nucleic acid encoding an immunogenic polypeptide having an amino acid sequence of SEQ ID NO: 17, and
- a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Weeks 26, 28, and 30, and 6 mg of the compound of Formula (I) is administered at Weeks 32, 34, 38, 40, 42, 44, and 46.

In some embodiments, the method of treating or preventing HIV infection in a human in need thereof suffering from HIV infection or at risk of developing HIV infection comprises administering to the human a compound of Formula (I):

(I)

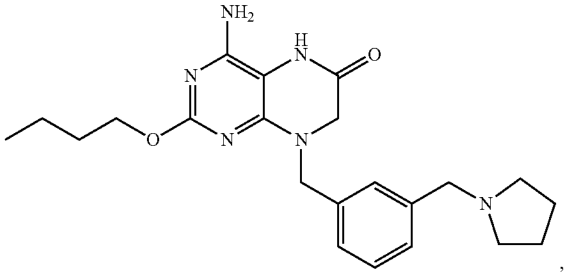

,

- a first virus comprising $5\times10^{10}$ viral particles of a replication-defective chimpanzee adenovirus comprising a nucleic acid encoding an immunogenic polypeptide having an amino acid sequence of SEQ ID NO: 17, and
- a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Weeks 26, 28, 30, and 32, and 6 mg of the compound of Formula (I) is administered at Weeks 34, 38, 40, 42, 44, and 46.

In some embodiments, the method of treating or preventing HIV infection in a human in need thereof suffering from HIV infection or at risk of developing HIV infection comprises administering to the human a compound of Formula (I):

(I)

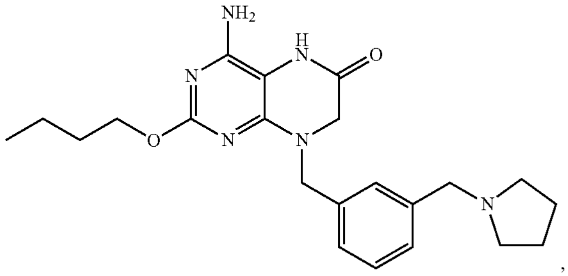

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, and 6 mg of the compound of Formula (I) is administered at Weeks 26, 28, 30, 32, 34, 38, 40, 42, 44, and 46.

In some embodiments, the method of treating or preventing HIV infection in a human in need thereof suffering from HIV infection or at risk of developing HIV infection comprises administering to the human a compound of Formula (I):

(I)

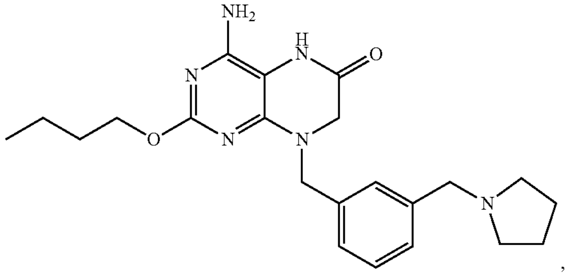

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 6 mg of the compound of Formula (I) is administered at Week 26 and Week 28, and 8 mg of the compound of Formula (I) is administered at Weeks 30, 32, 34, 38, 40, 42, 44, and 46.

In some embodiments, the method of treating HIV infection in a human in need thereof suffering from HIV infection comprises administering to the human a compound of Formula (I):

(I)

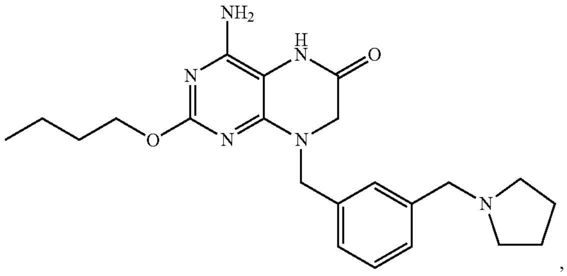

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 6 mg of the compound of Formula (I) is administered at Week 26 and Week 28, and 8 mg of the compound of Formula (I) is administered at Weeks 30, 32, 34, 38, 40, 42, 44, and 46.

A method comprising administering a compound of Formula (I) or a pharmaceutically acceptable salt thereof and an HIV vaccine described herein to a human is expected to to generate cellular and humoral responses against HIV in the human. In some embodiments, the vaccine generates an effective cytotoxic T cell response. A cytotoxic T cell or cytotoxic T lymphocyte (CTL) assay can be used to monitor the cellular immune response following subgenomic immunization with a viral sequence against homologous and heterologous HIV strains. See Burke, S. et al., J. Inf. Dis. 1994; 170:1110-1119 and Tigges, M. et al., J. Immunol, 1996; 156:3901-3910. Conventional assays utilized to detect T cell responses include, for instance, proliferation assays, lymphokine secretion assays, direct cytotoxicity assays and limiting dilution assays. For example, antigen-presenting cells that have been incubated with a peptide can be assayed for their ability to induce CTL responses in responder cell populations. Antigen-presenting cells can be cells such as peripheral blood mononuclear cells (PBMCs) or dendritic cells (DCs). Alternatively, mutant non-human mammalian cell lines that are deficient in their ability to load MHC class I molecules with internally processed peptides and that have been transfected with the appropriate human MHC class I gene, can be used to test the capacity of a peptide of interest to induce in vitro primary CTL responses. PBMCs can be used as the responder cell source of CTL precursors. The appropriate antigen-presenting cells are incubated with the peptide after which the protein-loaded antigen-presenting cells are incubated with the responder cell population under optimized culture conditions. Positive CTL activation can be determined by assaying the culture for the presence of CTL that kill radiolabeled target cells, both specific peptide-pulsed targets as well as target cells expressing endogenously processed forms of the antigen from which the peptide sequence was derived. For example, the target cells can be radiolabeled with $^{51}Cr$ and cytotoxic activity can be calculated from radioactivity released from the target cells. Another suitable method allows the direct quantification of antigen-specific T cells by staining with fluorescein-labeled HLA tetrameric complexes. See Altman J, et al., Proc. Natl. Acad. Sci. USA 1993; 90:10330-10334 and Altman J, et al., Science 1996; 274:94-96. Other relatively recent technical developments include staining for intracellular lymphokines and interferon release assays or ELISPOT assays. In some embodiments, a method of generating an effective CTL in a human in need thereof comprises administering to the human a therapeutically effective amount of a compound of the present disclosure and a virus encoding an immunogenic polypeptide comprises a sequence according to SEQ ID NOS: 1-16, wherein the CTL is directed to one or more of the following regions of an HIV virus: p17 17-94, p24 30-43, p24 61-71, p24 91-150, p24 164-177, p24 217-231, p2p7p1p6 63-89, protease 45-99, reverse transcriptase 34-50, reverse transcriptase 210-264, reverse transcriptase 309-342, integrase 210-243, integrase 266-282, Vif 25-50, Vif 166-184, and Nef 56-68, wherein the amino acid numbering is according to HIV-1 HXB2.

Also provided is a method of enhancing the efficacy of an HIV vaccine, the method comprising administering to a human in need thereof a pharmaceutically effective amount of a TLR7 modulating compound of Formula (I) or a pharmaceutically acceptable salt thereof and an HIV vaccine as described herein.

A clinical improvement of a treated HIV-infected human above a comparator HIV-infected human treated with a standard of care is expected. The clinical improvement can include one or more of a lower peak viral load, a lower chronic set point, or an increased delay in viral rebound.

In some embodiments, the method as described herein has an effect on treatment of the HIV infection, for example, as determined by a lower peak viral load as compared to standard therapies, e.g., ART only. As is commonly understood in the art, comparison of a first peak viral load in a first HIV-infected human and a second peak viral load in a second HIV-infected human is measured during the same time period. In some embodiments, the measurement is performed after cessation of all antiviral therapies. In some embodiments, the viral load is maintained at an undetectable level in a first HIV-infected human after treatment with ART, a TLR7 modulating compound, and an HIV vaccine.

In some embodiments, a first peak viral load in a first HIV-infected human after treatment with ART, a TLR7 modulating compound, and an HIV vaccine is lower than a second peak viral load in a second HIV-infected human after treatment with ART only. In some embodiments, the second peak viral load in a second HIV-infected human after treatment with ART only is higher, e.g., from about 1.2 to about 10000 times, from about 2 to about 10000 times, from about 5 to about 10000 times, from about 10 to about 10000 times, higher, than the first peak viral load in a first HIV-infected human after treatment with ART, a TLR7 modulating compound, and an HIV vaccine. In some embodiments, the second peak viral load in a second HIV-infected human after treatment with ART only is about 1.2, about 1.5, about 2, about 3, about 4, about 5, about 10, about 20, about 50, about 100, about 200, about 500, about 1000, about 2000, about 5000, or about 10000 times higher than the first peak viral load in a first HIV-infected human after treatment with ART, a TLR7 modulating compound, and an HIV vaccine. In some embodiments, the second peak viral load in a second HIV-infected human after treatment with ART only is about 1000 times higher than the first peak viral load in a first HIV-infected human after treatment with ART, a TLR7 modulating compound, and an HIV vaccine.

In some embodiments, a first peak viral load in a first HIV-infected human after treatment with ART, a TLR7 modulating compound, and an HIV vaccine is lower than a second peak viral load in a second HIV-infected human after treatment with ART and the TLR7 modulating compound. In some embodiments, the second peak viral load in a second HIV-infected human after treatment with ART and the TLR7 modulating compound is higher, e.g., from about 1.2 to about 10000 times, from about 2 to about 10000 times, from about 5 to about 10000 times, from about 10 to about 10000 times, higher, than the first peak viral load in a first HIV-infected human after treatment with ART, a TLR7 modulating compound, and an HIV vaccine. In some embodiments, the second peak viral load in a second HIV-infected human after treatment with ART and the TLR7 modulating compound is about 1.2, about 1.5, about 2, about 3, about 4, about 5, about 10, about 20, about 50, about 100, about 200, about 500, about 1000, about 2000, about 5000, or about 10000 times higher than the first peak viral load in a first HIV-infected human after treatment with ART, a TLR7 modulating compound, and an HIV vaccine. In some embodiments, the second peak viral load in a second HIV-infected human after treatment with ART and the TLR7 modulating compound is about 20 times higher than the first peak viral load in a first HIV-infected human after treatment with ART, a TLR7 modulating compound, and an HIV vaccine.

In some embodiments, a first peak viral load in a first HIV-infected human after treatment with ART, a TLR7 modulating compound, and an HIV vaccine is lower than a second peak viral load in a second HIV-infected human after treatment with ART and the HIV vaccine. In some embodiments, the second peak viral load in a second HIV-infected human after treatment with ART and the HIV vaccine is higher, e.g., from about 1.2 to about 10000 times, from about 2 to about 10000 times, from about 5 to about 10000 times, from about 10 to about 10000 times, higher, than the first peak viral load in a first HIV-infected human after treatment with ART, a TLR7 modulating compound, and an HIV vaccine. In some embodiments, the second peak viral load in a second HIV-infected human after treatment with ART and the HIV vaccine is about 1.2, about 1.5, about 2, about 3, about 4, about 5, about 10, about 20, about 50, about 100, about 200, about 500, about 1000, about 2000, about 5000, or about 10000 times higher than the first peak viral load in a first HIV-infected human after treatment with ART, a TLR7 modulating compound, and an HIV vaccine. In some embodiments, the second peak viral load in a second HIV-infected human after treatment with ART and the HIV vaccine is about 100 times higher than the first peak viral load in a first HIV-infected human after treatment with ART, a TLR7 modulating compound, and an HIV vaccine.

In some embodiments, the method as described herein has an effect on treatment of the HIV infection, for example, as determined by a lower chronic set point as compared to standard therapies, e.g., ART. As is commonly understood in the art, comparison of a first chronic set point in a first HIV-infected human and a second chronic set point in a second HIV-infected human is measured at the same time point. In some embodiments, the measurement is performed after cessation of all antiviral therapies.

In some embodiments, a first chronic set point in a first HIV-infected human after treatment with ART, a TLR7 modulating compound, and an HIV vaccine is lower than a second chronic set point in a second HIV-infected human after treatment with ART only. In some embodiments, the second chronic set point in a second HIV-infected human after treatment with ART only is higher, e.g., from about 1.2 to about 10000 times, from about 2 to about 10000 times, from about 5 to about 10000 times, from about 10 to about 10000 times, higher, than the first chronic set point in a first HIV-infected human after treatment with ART, a TLR7 modulating compound, and an HIV vaccine. In some embodiments, the second chronic set point in a second HIV-infected human after treatment with ART only is about 1.2, about 1.5, about 2, about 3, about 4, about 5, about 10, about 20, about 50, about 100, about 200, about 500, about 1000, about 2000, about 5000, or about 10000 times higher than the first chronic set point in a first HIV-infected human after treatment with ART, a TLR7 modulating compound, and an HIV vaccine. In some embodiments, the second chronic set point in a second HIV-infected human after treatment with ART only is about 10 times higher than the first chronic set point in a first HIV-infected human after treatment with ART, a TLR7 modulating compound, and an HIV vaccine.

In some embodiments, a first chronic set point in a first HIV-infected human after treatment with ART, a TLR7 modulating compound, and an HIV vaccine is lower than a second chronic set point in a second HIV-infected human after treatment with ART and the TLR7 modulating compound. In some embodiments, the second chronic set point in a second HIV-infected human after treatment with ART and the TLR7 modulating compound is higher, e.g., from about 1.2 to about 10000 times, from about 2 to about 10000 times, from about 5 to about 10000 times, from about 10 to about 10000 times, higher, than the first chronic set point in a first HIV-infected human after treatment with ART, a TLR7 modulating compound, and an HIV vaccine. In some embodiments, the second chronic set point in a second HIV-infected human after treatment with ART and the TLR7 modulating compound is about 1.2, about 1.5, about 2, about 3, about 4, about 5, about 10, about 20, about 50, about 100, about 200, about 500, about 1000, about 2000, about 5000, or about 10000 times higher than the first chronic set point in a first HIV-infected human after treatment with ART, a TLR7 modulating compound, and an HIV vaccine. In some embodiments, the second chronic set point in a second HIV-infected human after treatment with ART and the TLR7 modulating compound is about 2 times higher than the first chronic set point in a first HIV-infected human after treatment with ART, a TLR7 modulating compound, and an HIV vaccine.

In some embodiments, a first chronic set point in a first HIV-infected human after treatment with ART, a TLR7 modulating compound, and an HIV vaccine is lower than a second chronic set point in a second HIV-infected human after treatment with ART and the HIV vaccine. In some embodiments, the second chronic set point in a second HIV-infected human after treatment with ART and the HIV vaccine is higher, e.g., from about 1.2 to about 10000 times, from about 2 to about 10000 times, from about 5 to about 10000 times, from about 10 to about 10000 times, higher, than the first chronic set point in a first HIV-infected human after treatment with ART, a TLR7 modulating compound, and an HIV vaccine. In some embodiments, the second chronic set point in a second HIV-infected human after treatment with ART and the HIV vaccine is about 1.2, about 1.5, about 2, about 3, about 4, about 5, about 10, about 20, about 50, about 100, about 200, about 500, about 1000, about 2000, about 5000, or about 10000 times higher than the first chronic set point in a first HIV-infected human after treatment with ART, a TLR7 modulating compound, and an HIV vaccine. In some embodiments, the second chronic set point in a second HIV-infected human after treatment with ART and the HIV vaccine is about 10 times higher than the first chronic set point in a first HIV-infected human after treatment with ART, a TLR7 modulating compound, and an HIV vaccine.

The instant method can increase the delay in viral rebound as compared to standard therapies after cessation of all antiviral therapies. In some embodiments, the viral load does not rebound in an HIV-infected human after treatment with ART, a TLR7 modulating compound, and an HIV vaccine. In the case of no rebound, the previously HIV-infected human maintains an undetectable viral load after cessation of antiviral therapies for at least 1 month, 2 months, 3 months, 4 months, 5 months, 6 months, 7 months, 8 months, 9 months, 10 months, 11 months, 1 year, 1.5 years, 2 years, 3 years, 5 years, or at least 10 years or longer after antiviral therapies have ceased.

In some embodiments, a first delay in viral rebound in a first HIV-infected human after treatment with ART, a TLR7 modulating compound, and an HIV vaccine is longer than a second delay in viral rebound in a second HIV-infected human after treatment with ART only. In some embodiments, a first delay in viral rebound in a first HIV-infected human after treatment with ART, a TLR7 modulating compound, and an HIV vaccine is from about 1 day to about 10 years, e.g., from about 1 week to about 1 year, from about 2 weeks to about 1 year, from about 3 weeks to about 1 year, from about 1 month to about 1 year, from about 2 months to about 1 year, from about 3 months to about 1 year, from about 3 months to about 2 years, etc., longer compared to a second delay in viral rebound in a second HIV-infected human after treatment with ART only. In some embodiments, a first delay in viral rebound in a first HIV-infected human after treatment with ART, a TLR7 modulating compound, and an HIV vaccine is greater than 1 day, 3 days, 1 week, 2 weeks, 3 weeks, 1 month, 2 months, 3 months, 4 months, 5 months, 6 months, 7 months, 8 months, 9 months, 10 months, 11 months, 1 year, 1.5 years, 2 years, 3 years, 5 years, 10 years or longer compared to a second delay in viral rebound in a second HIV-infected human after treatment with ART only. In some embodiments, a first delay in viral rebound in a first HIV-infected human after treatment with ART, a TLR7 modulating compound, and an HIV vaccine is about 1 week, about 2 weeks, about 3 weeks, about 1 month, about 2 month, about 3 months, about 4 months, about 5 months, about 6 months, about 7 months, about 8 months, about 9 months, about 10 months, about 11 months, about 1 year, about 1.5 years, about 2 years, about 3 years or longer compared to a second delay in viral rebound in a second HIV-infected human after treatment with ART only. In some embodiments, a first delay in viral rebound in a first HIV-infected human after treatment with ART, a TLR7 modulating compound, and an HIV vaccine is about 3 months longer compared to a second delay in viral rebound in a second HIV-infected human after treatment with ART only.

In some embodiments, a first delay in viral rebound in a first HIV-infected human after treatment with ART, a TLR7 modulating compound, and an HIV vaccine is longer than a second delay in viral rebound in a second HIV-infected human after treatment with ART and the TLR7 modulating compound. In some embodiments, a first delay in viral rebound in a first HIV-infected human after treatment with ART, a TLR7 modulating compound, and an HIV vaccine is from about 1 day to about 10 years, e.g., from about 1 week to about 1 year, from about 2 weeks to about 1 year, from about 3 weeks to about 1 year, from about 1 month to about 1 year, from about 2 months to about 1 year, from about 3 months to about 1 year, from about 3 months to about 2 years, etc., longer compared to a second delay in viral rebound in a second HIV-infected human after treatment with ART and the TLR7 modulating compound. In some embodiments, a first delay in viral rebound in a first HIV-infected human after treatment with ART, a TLR7 modulating compound, and an HIV vaccine is greater than 1 day, 3 days, 1 week, 2 weeks, 3 weeks, 1 month, 2 month, 3 months, 4 months, 5 months, 6 months, 7 months, 8 months, 9 months, 10 months, 11 months, 1 year, 1.5 years, 2 years, 3 years or longer compared to a second delay in viral rebound in a second HIV-infected human after treatment with ART and the TLR7 modulating compound. In some embodiments, a first delay in viral rebound in a first HIV-infected human after treatment with ART, a TLR7 modulating compound, and an HIV vaccine is about 1 week, about 2 weeks, about 3 weeks, about 1 month, about 2 month, about 3 months, about 4 months, about 5 months, about 6 months, about 7 months, about 8 months, about 9 months, about 10 months, about 11 months, about 1 year, about 1.5 years, about 2 years, about 3 years or longer compared to a second delay in viral rebound in a second HIV-infected human after treatment with ART and the TLR7 modulating compound. In some embodiments, a first delay in viral rebound in a first HIV-infected human after treatment with ART, a TLR7 modulating compound, and an HIV vaccine is about 3 months longer compared to a second delay in viral rebound in a second HIV-infected human after treatment with ART and the TLR7 modulating compound.

In some embodiments, a first delay in viral rebound in a first HIV-infected human after treatment with ART, a TLR7 modulating compound, and an HIV vaccine is longer than a second delay in viral rebound in a second HIV-infected human after treatment with ART and the HIV vaccine. In some embodiments, a first delay in viral rebound in a first HIV-infected human after treatment with ART, a TLR7 modulating compound, and an HIV vaccine is from about 1 day to about 10 years, e.g., from about 1 week to about 1 year, from about 2 weeks to about 1 year, from about 3 weeks to about 1 year, from about 1 month to about 1 year, from about 2 months to about 1 year, from about 3 months to about 1 year, from about 3 months to about 2 years, etc., longer compared to a second delay in viral rebound in a second HIV-infected human after treatment with ART and the HIV vaccine. In some embodiments, a first delay in viral rebound in a first HIV-infected human after treatment with ART, a TLR7 modulating compound, and an HIV vaccine is greater than 1 day, 3 days, 1 week, 2 weeks, 3 weeks, 1 month, 2 month, 3 months, 4 months, 5 months, 6 months, 7 months, 8 months, 9 months, 10 months, 11 months, 1 year, 1.5 years, 2 years, 3 years or longer compared to a second delay in viral rebound in a second HIV-infected human after treatment with ART and the HIV vaccine. In some embodiments, a first delay in viral rebound in a first HIV-infected human after treatment with ART, a TLR7 modulating compound, and an HIV vaccine is about 1 week, about 2 weeks, about 3 weeks, about 1 month, about 2 month, about 3 months, about 4 months, about 5 months, about 6 months, about 7 months, about 8 months, about 9 months, about 10 months, about 11 months, about 1 year, about 1.5 years, about 2 years, about 3 years or longer compared to a second delay in viral rebound in a second HIV-infected human after treatment with ART and the HIV vaccine. In some embodiments, a first delay in viral rebound in a first HIV-infected human after treatment with ART, a TLR7 modulating compound, and an HIV vaccine is about 1 month longer compared to a second delay in viral rebound in a second HIV-infected human after treatment with ART and the HIV vaccine.

VII. Administration

The combination of a TLR7 modulating compound of the present disclosure, e.g., a compound of Formula (I), or a pharmaceutically acceptable salt thereof, and an HIV vaccine as described herein is administered to a human to increase the likelihood of achieving the desired biological effect and to minimize adverse effects. In some embodiments, the TLR7 modulating compound and the HIV vaccine is administered concurrently. In some embodiments, the TLR7 modulating compound and the HIV vaccine is administered sequentially, e.g., on different days or different weeks.

An HIV vaccine as described herein can be administered by any means known in the art, including but not limited to intravenous, intramuscular, intrathecal, intraperitoneal, intranasal, or oral administration. In some embodiments, the HIV vaccine is administered intramuscularly. In some embodiments, the HIV vaccine is administered once every 8, 10, 12, 14, or 16 weeks. In some embodiments, the HIV vaccine is administered once every 12 weeks. In some embodiments, the HIV vaccine comprises a first virus and a second virus. In some embodiments, the first virus is administered one or more times, then the second virus is administered one or more times. In some embodiments, the first virus is administered twice, and the second virus is administered twice. In some embodiments, the first virus is administered at Week 0 and Week 12, and the second virus is administered at Week 24 and Week 36.

A TLR7 modulating compound of the present disclosure can be administered by any means known in the art, including but not limited to intravenous, intramuscular, intrathecal, intraperitoneal, or oral administration. In some embodiments, the TLR7 modulating compound is administered orally.

In some embodiments, the TLR7 modulating compound of Formula (I) or a pharmaceutically acceptable salt thereof is administered once every week, every two weeks, or every three weeks. In some embodiments, the compound of Formula (I) or a pharmaceutically acceptable salt thereof is administered once every two weeks, e.g., every 12-16, 13-15, or 14 days. In some embodiments, the compound of Formula (I) or a pharmaceutically acceptable salt thereof is administered every two weeks after the third administration of virus. In some embodiments, the compound of Formula (I) or a pharmaceutically acceptable salt thereof is administered in a continuous manner, e.g., once every two weeks over eight weeks for a total of 5 administrations, i.e., at Weeks 26, 28, 30, 32, and 34, wherein Week 0 is the initial administration of the first virus. In some embodiments, the compound of Formula (I) or a pharmaceutically acceptable salt thereof is administered intermittently. In some embodiments, the compound of Formula (I) or a pharmaceutically acceptable salt thereof is administered at Weeks 26, 28, 30, 32, 34, 38, 40, 42, 44, and 46, wherein Week 0 is the initial administration of the first virus.

In some embodiments, a compound of Formula (I) is administered as a single tablet. In some embodiments, a compound of Formula (I) is administered in two or more, e.g., 3, 4, or 5, tablets. When administered as two or more tablets, the compound of Formula (I) can be present at the same dose, e.g., three tablets of 2 mg (i.e., 3×2 mg) of the compound of Formula (I) for a total of 6 mg administered, or two tablets of 4 mg of the compound of Formula (I) for a total of 8 mg administered, or at different doses, e.g., one tablet of 4 mg of the compound of Formula (I) and one tablet of 2 mg of the compound of Formula (I) for a total of 6 mg administered.

In some embodiments, from about 4 mg to about 12 mg, such as from about 6 to about 8 mg, e.g., about 4, 5, 6, 7, 8, 9, 10. 11, or about 12 mg, of the compound of Formula (I) or a pharmaceutically acceptable salt thereof is administered. In some embodiments, the compound of Formula (I) or a pharmaceutically acceptable salt thereof is administered 10 times. In some embodiments, the compound of Formula (I) or a pharmaceutically acceptable salt thereof is administered in 10 doses, with one 4 mg tablet for doses 1-2 and 3×2 mg tablets for doses 3-10. In some embodiments, the compound of Formula (I) or a pharmaceutically acceptable salt thereof is administered in 10 doses, with one 4 mg tablet for doses 1-3 and 3×2 mg tablets for doses 4-10. In some embodiments, the compound of Formula (I) or a pharmaceutically acceptable salt thereof is administered in 10 doses, with one 4 mg tablet for doses 1-4 and 3×2 mg tablets for doses 5-10. In some embodiments, the compound of Formula (I) or a pharmaceutically acceptable salt thereof is administered in 10 doses, with 3×2 mg tablets for doses 1-10. In some embodiments, the compound of Formula (I) or a pharmaceutically acceptable salt thereof is administered in 10 doses, with 3×2 mg tablets for doses 1-2 and 2×4 mg tablets for doses 3-10. In some embodiments, the compound of Formula (I) or a pharmaceutically acceptable salt thereof is administered in 10 doses, with 5×2 mg tablets for doses 1-3 and 3×4 mg tablets for doses 4-10.

In some embodiments, the TLR7 modulating compound of Formula (I) or a pharmaceutically acceptable salt thereof and an HIV vaccine is administered concurrently with ART. In some embodiments, the therapeutic agents of the ART are the same before and during administration of the compound of Formula (I) and the HIV vaccine. In some embodiments, the therapeutic agents of the ART are different before and during administration of the compound of Formula (I) and the HIV vaccine.

In some embodiments, a method comprises administering to a human a therapeutically effective amount of a compound of Formula (I):

(I)

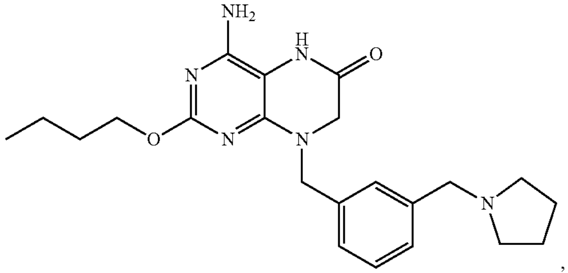

, or a pharmaceutically acceptable salt thereof, and a first virus comprising an immunogenic polypeptide, or a nucleic acid encoding an immunogenic polypeptide, wherein the immunogenic polypeptide comprises:

(i) a sequence having at least 90%, 91%, 92%, 93%, 94%, 95%, 96%, 97%, 98%, or 99% sequence identity to SEQ ID NO: 1;

(ii) a sequence having at least 90%, 91%, 92%, 93%, 94%, 95%, 96%, 97%, 98%, or 99% sequence identity to SEQ ID NO: 2;

(iii) a sequence having at least 90%, 91%, 92%, 93%, 94%, 95%, 96%, 97%, 98%, or 99% sequence identity to SEQ ID NO: 3;

(iv) a sequence having at least 90%, 91%, 92%, 93%, 94%, 95%, 96%, 97%, 98%, or 99% sequence identity to SEQ ID NO: 4;

(v) a sequence having at least 90%, 91%, 92%, 93%, 94%, 95%, 96%, 97%, 98%, or 99% sequence identity to SEQ ID NO: 5;

(vi) a sequence having at least 90%, 91%, 92%, 93%, 94%, 95%, 96%, 97%, 98%, or 99% sequence identity to SEQ ID NO: 6;

(vii) a sequence having at least 90%, 91%, 92%, 93%, 94%, 95%, 96%, 97%, 98%, or 99% sequence identity to SEQ ID NO: 7;

(viii) a sequence having at least 90%, 91%, 92%, 93%, 94%, 95%, 96%, 97%, 98%, or 99% sequence identity to SEQ ID NO: 8;

(ix) a sequence having at least 90%, 91%, 92%, 93%, 94%, 95%, 96%, 97%, 98%, or 99% sequence identity to SEQ ID NO: 9;

(x) a sequence having at least 90%, 91%, 92%, 93%, 94%, 95%, 96%, 97%, 98%, or 99% sequence identity to SEQ ID NO: 10;

(xi) a sequence having at least 90%, 91%, 92%, 93%, 94%, 95%, 96%, 97%, 98%, or 99% sequence identity to SEQ ID NO: 11;

(xii) a sequence having at least 90%, 91%, 92%, 93%, 94%, 95%, 96%, 97%, 98%, or 99% sequence identity to SEQ ID NO: 12;

(xiii) a sequence having at least 90%, 91%, 92%, 93%, 94%, 95%, 96%, 97%, 98%, or 99% sequence identity to SEQ ID NO: 13;

(xiv) a sequence having at least 90%, 91%, 92%, 93%, 94%, 95%, 96%, 97%, 98%, or 99% sequence identity to SEQ ID NO: 14;

(xv) a sequence having at least 90%, 91%, 92%, 93%, 94%, 95%, 96%, 97%, 98%, or 99% sequence identity to SEQ ID NO: 15; and (xvi) a sequence having at least 90%, 91%, 92%, 93%, 94%, 95%, 96%, 97%, 98%, or 99% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85, e.g., from 11 to 82, from 11 to 80, or from 11 to 78, amino acids in length. In some embodiments, the immunogenic polypeptide comprises a sequence having amino acid sequences with no more than 1, 2, or 3 substitutions in any one of SEQ ID NOS: 1-16. In some embodiments, the immunogenic polypeptide comprises a sequence having amino acid sequences according to SEQ ID NOS: 1-16.

In some embodiments, the immunogenic polypeptide that comprises an amino acid sequence having at least 90%, 91%, 92%, 93%, 94%, 95%, 96%, 97%, 98%, or 99% sequence identity to SEQ ID NO: 17 is administered. In some embodiments, the immunogenic polypeptide comprises an amino acid sequence according to SEQ ID NO: 17.

In some embodiments, the nucleic acid encoding the immunogenic polypeptide that comprises a nucleic acid sequence having at least 90%, 91%, 92%, 93%, 94%, 95%, 96%, 97%, 98%, or 99% sequence identity to SEQ ID NO:

18 is administered. In some embodiments, the nucleic acid encoding the immunogenic polypeptide comprises a nucleic acid sequence according to SEQ ID NO: 18.

In some embodiments, a method comprises administering to a human a compound of Formula (I):

(I)

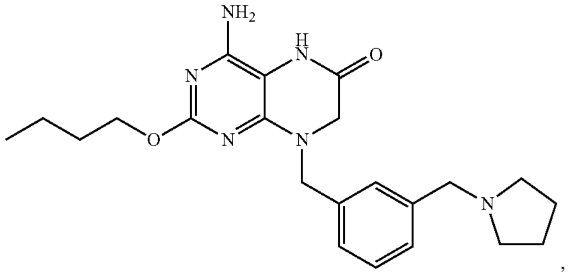

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Week 26 and Week 28, and 6 mg of the compound of Formula (I) is administered at Weeks 30, 32, 34, 38, 40, 42, 44, and 46.

In some embodiments, a method comprises administering to a human a compound of Formula (I):

(I)

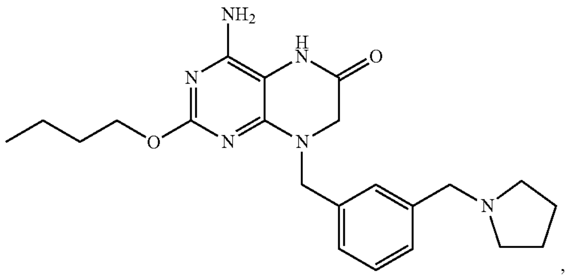

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Weeks 26, 28, and 30, and 6 mg of the compound of Formula (I) is administered at Weeks 32, 34, 38, 40, 42, 44, and 46.

In some embodiments, a method comprises administering to a human a compound of Formula (I):

(I)

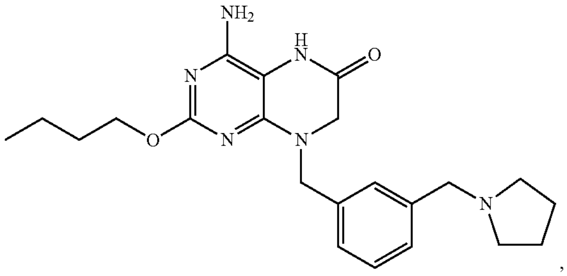

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 4 mg of the compound of Formula (I) is administered at Weeks 26, 28, 30, and 32, and 6 mg of the compound of Formula (I) is administered at Weeks 34, 38, 40, 42, 44, and 46.

In some embodiments, a method comprises administering to a human a compound of Formula (I):

(I)

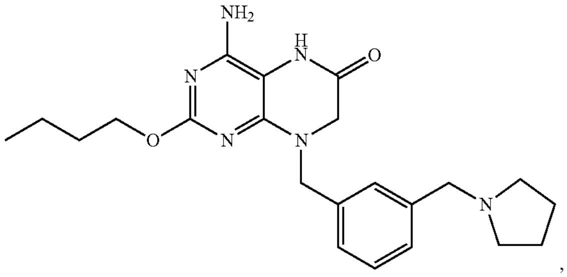

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, and 6 mg of the compound of Formula (I) is administered at Weeks 26, 28, 30, 32, 34, 38, 40, 42, 44, and 46.

In some embodiments, a method comprises administering to a human a compound of Formula (I):

(I)

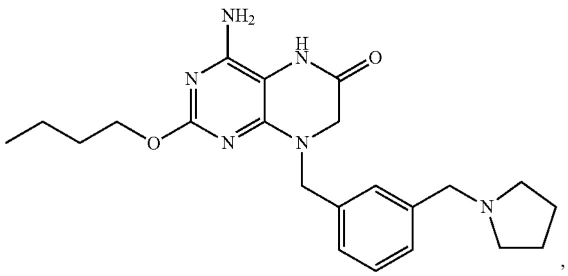

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 6 mg of the compound of Formula (I) is administered at Week 26 and Week 28, and 8 mg of the compound of Formula (I) is administered at Weeks 30, 32, 34, 38, 40, 42, 44, and 46.

VIII. Kits

The present disclosure provides a kit comprising a TLR7 modulating compound of Formula (I) or a pharmaceutically acceptable salt thereof and an HIV vaccine as described herein. The kit may further comprise instructions for use, e.g., for use in treating a viral infection. The instructions for use are generally written instructions, although electronic storage media (e.g., magnetic diskette or optical disk) containing instructions are also acceptable.

The present disclosure also provides a pharmaceutical kit comprising one or more containers comprising a compound of Formula (I) or a pharmaceutically acceptable salt thereof, and an HIV vaccine. Optionally associated with such container(s) can be a notice in the form prescribed by a governmental agency regulating the manufacture, use or sale of pharmaceuticals, which notice reflects approval by the agency for the manufacture, use or sale for human administration. Each component can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and the HIV vaccines with instructions for use and be packaged in quantities sufficient for storage and use in pharmacies (e.g., hospital pharmacies and compounding pharmacies).

Also provided are articles of manufacture comprising a unit dosage of a compound of the present disclosure or a pharmaceutically acceptable salt thereof, and an HIV vaccine, in suitable packaging for use in the methods described herein. Suitable packaging is known in the art and includes, for example, vials, vessels, ampules, bottles, jars, flexible packaging and the like. An article of manufacture may further be sterilized and/or sealed.

IX. Examples

Example 1. HIV Treatment Protocol of a TLR7 Modulating Compound of Formula (I) and an HIV Vaccine A Phase IIa, randomized, double-blind, double-dummy, placebo-controlled study evaluating the safety and tolerability of the sequential regimen of HIV vaccine and the compound of Formula (I) in early diagnosed and early treated HIV-1 infection is described in this Example. The study screens HIV-1 infected participants who have initiated ART within 180 days (6 months) of the estimated date of HIV-1 acquisition and who have achieved virological suppression for at least 1 year. Participants who provide informed consent and meet study entry criteria are randomized into 1 of 4 parallel treatment groups. The study is conducted in 3 periods: Period 1 lasts 48 weeks during which participants receive the administration regimen and continue the ART regimen; Period 2 lasts up to 24 weeks during which participants discontinue the ART regimen (i.e., analytical treatment interruption period); and Period 3 lasts up to 12 weeks during which participants are monitored following the restart of their ART.

The following criteria for a participant to be enrolled in the study includes that the patient:

(1) Is from 18 to 60 years old with a confirmed HIV-1 infection;

(2) Is receiving ART, i.e., three or more anti-retroviral drugs, that was initiated within 6 months of the estimated date of HIV-1 acquisition. Early treatment initiation needs to be documented by at least 1 of the following criteria (a)-(h):

(a) Third or fourth generation assay for HIV-1/2 negative and positive plasma HIV-1 RNA<160 days before ART initiation date, (b) Third generation assay for HIV1/2 negative and positive plasma HIV-1 p24Ag and positive plasma HIV-1 RNA<158 days before ART initiation date, (c) Fourth generation assay for HIV1/2 positive and negative HIV-1 and 2 antibody differentiation immunoassay and positive HIV-1 RNA<158 days before ART initiation date, (d) Third or fourth generation assay for HIV-1/2 positive and negative Western blot (WB) test (no bands detected) and positive HIV-1 RNA<157 days before ART initiation date, (e) Third or fourth generation assay for HIV-1/2 positive and indeterminate WB test (<2 envelope bands) and positive HIV-1 RNA<151 days before ART initiation date, (f) Third or fourth generation assay for HIV-1/2 positive and indeterminate HIV-1 and 2 antibody differentiation immunoassay and positive HIV-1 RNA, (g) HIV seroconversion (negative HIV test<160 days before the first positive HIV test) and ART initiated <90 days since HIV-1 diagnosis, and (h) Third or fourth generation assay for HIV-1/2 positive and positive WB test without the p31 band <90 days before ART initiation date, in the context of a compatible medical history (either by a clear reported risk of transmission and/or documented acute retroviral syndrome <5 months before HIV diagnosis)<151 days before ART initiation date;

(3) Has been virologically suppressed, defined as pVL<50 copies/mL, for at least 1 year before screening; isolated blips allowed (<200 copies/mL, non-consecutive, representing <10% of total determinations or occurrence less than or equal to twice per year);

(4) Has stable CD4 counts >450 cells/$mm^3$ for the 6 months before screening; and (5) Has nadir CD4 count >200 cells/mm$^3$ since HIV diagnosis; isolated lower counts at the moment of acute HIV-1 infection will be allowed only if appropriate immune recovery was followed after ART initiation (see inclusion criterion #4).

Participants are screened to be enrolled in the study. After providing informed consent, participants are randomly assigned in a 5:1:1:2 ratio using an interactive response technology (IRT) to receive the HIV vaccine and the compound of Formula (I), the HIV vaccine only, the compound of Formula (I) only, or placebo. Randomization is stratified by sentinel and non-sentinel participants. A sentinel cohort consisting of the first 9 participants is randomized 5:1:1:2 and dosed. A blinded, independent Safety Monitoring Committee (SMC) reviews the sentinel cohort data collected through 1 week after the last sentinel participant has received his/her first injection, before enrollment of the remaining 81 participants (non-sentinel cohort). The SMC reviews the safety data for all participants for the remainder of the study. Sentinel participants who discontinue the study, for reasons unrelated to safety, within 1 week after the first Investigational Medicinal Product (IMP) dose are replaced, while sentinel participants who discontinue the study after this time point and non-sentinel participants who discontinue the study after first IMP dose are not replaced. The IMP administration schedule will be managed by the IRT.

Because the compound of Formula (I) is predominantly metabolized by cytochrome P450 (CYP) 3A4 enzyme (CYP3A) with minor contributions from CYP2C8 and CYP2D6 in vitro and because the compound of Formula (I) is a substrate of P-glycoprotein and breast cancer resistance protein in vitro, compound plasma exposures may increase or decrease when co-administered with CYP3A, P-glycoprotein, or breast cancer resistance protein inhibitors or inducers. Any ART agents known to inhibit or induce CYP3A, P-glycoprotein, or breast cancer resistance protein are excluded from use in this study during treatment (Period 1). For those participants who may be on a regimen including one of these medications, a regimen switch from one of the prohibited medication to an allowed medication is permitted between the screening and baseline visits. The following agents are excluded from the ART regimen during the study: HIV protease inhibitors (including low-dose ritonavir), cobicistat-containing regimens, elvitegravir, efavirenz, etravirine, and nevirapine.

Participants have a screening visit within 28 days before the first dose of HIV vaccine. In Period 1 (Week 0 to Week 48), participants are randomly assigned to treatment at Week 0 (baseline) and receive the first dose of HIV vaccine or matched vaccine placebo administration on the same day. Participants who need to switch their ART from a prohibited medication to one allowed during the study does so between screening and baseline and for these participants the screening period is extended up to 45 days before the first dose.

Participants continue to take ART during Period 1. Participants in the sentinel cohort have additional Period 1 visits compared with the non-sentinel cohort for additional monitoring and assessments. Participants receive an HIV vaccine comprising a first virus and a second virus: up to two doses of a first virus comprising $5\times10^{10}$ viral particles in 0.5 mL formulation buffer of a replication-defective chimpanzee adenovirus comprising a nucleic acid encoding an immunogenic polypeptide having an amino acid sequence of SEQ ID NO: 17, two doses of a second virus comprising $2\times10^{8}$ plaque-forming units in 0.5 mL Tris buffer of a modified vaccinia virus Ankara (MVA) comprising a nucleic acid encoding an immunogenic polypeptide having an amino acid sequence of SEQ ID NO: 17, and ten doses of the compound of Formula (I), or matching placebos during Period 1. All participants have HIV-1 viral loads monitored throughout Period 1. At the end of Period 1, participants meet analytical treatment interruption (ATI) eligibility criteria before entering Period 2 to start ATI. If ATI eligibility criteria are not met, entry into Period 2 is postponed or the participant is discontinued from the study and undergoes Period 1 Early Termination procedures. Participants in Period 1 who prematurely discontinue vaccine are withdrawn from the study and complete the Period 1 Early Termination assessments, while participants who prematurely discontinue compound administration have the option to continue in the study and proceed to Period 2.

The first virus comprises a replication-defective recombinant chimpanzee adenovirus (ChAd) vector based on a chimpanzee adenoviral isolate ChAdY25 described in U.S. Pat. No. 9,714,435 (incorporated herein by reference in its entirety), wherein the vector encodes the immunogenic polypeptide according to SEQ ID NO:17. The vector is derived by sub-cloning the immunogenic polypeptide sequence into the generic ChAdOx1 bacterial artificial chromosome (BAC) system (Oxford University, Oxford, United Kingdom). The plasmid resulting from this sub-cloning (pC255; 40,483 kbp) is linearized and transfected into commercial HEK293 T-REx® cells (Thermo Fisher Scientific, Waltham, Mass. USA) to produce the first virus, which is formulated as a suspension for intramuscular injection. The buffer for injection contains 10 mM L-Histidine, 35 mM NaCl, 7.5% (w/v) sucrose, 1 mM $MgCl_2$, 0.1 mM EDTA disodium, 0.1% (w/v) Polysorbate-80, and 0.5% (v/v) ethanol. The pH is adjusted to 6.6 with HCl. Vials are stored at −80° C.

The schedule for administration in Period 1 is as follows: At Weeks 0 and 12, a first virus comprising $5\times10^{10}$ viral particles in 0.5 mL formulation buffer of a replication-defective chimpanzee adenovirus comprising a nucleic acid encoding an immunogenic polypeptide having an amino acid sequence of SEQ ID NO: 17 is administered. At Weeks 24 and 36, a second virus comprising $2\times10^{8}$ plaque-forming units in 0.5 mL Tris buffer (10 mM Tris HCl, pH 7.7, 140 mM NaCl) of a modified vaccinia virus Ankara (MVA) comprising a nucleic acid encoding an immunogenic polypeptide having an amino acid sequence of SEQ ID NO: 17 is administered. At Weeks 26 and 28, 6 mg of a compound of Formula (I) is administered. At Weeks 30, 32, 34, 38, 40, 42, 44, and 46, 8 mg of a compound of Formula (I) is administered, provided that no compound-related Grade 3/4 adverse event occurs upon administration of 6 mg of the compound.

In Period 2 (Week 48 to Week 72), participants are instructed to discontinue ART after the Week 48 visit. Participants are monitored at weekly visits for rebound in HIV-1 plasma viremia. Participants have their ART restarted during Period 2 if specific criteria are met. Participants who have a viral load <50 copies/mL at the end of Period 2 and who have not restarted ART during Period 2 have additional assessments performed at the Week 72 visit. Participants who meet criteria for restarting ART during Period 2 have ART restarted and the participant enters Period 3. If a participant prematurely discontinues from the study during Period 2, the participant's ART regimen should be restarted and the participant should undergo Period 2 Early Termination procedures.

The 24-week Period 2 consists of weekly visits. Participants discontinue their use of ART at Week 48. All participants restart ART once they have met the criteria for doing so or at the Week 72 visit at the latest. All participants who restart their ART prior to the end of Period 2 continue to Period 3 at the time their ART medications are restarted. All participants who restart their ART during Period 2, whether during Period 2 or at the end of Period 2 (i.e., during Week 72), have their viral load monitored after restarting ART.

During Period 2, careful clinical monitoring of symptoms is performed by the investigator. Participants provide regular blood samples for determining HIV-1 pVL (i.e., plasma viral load), CD4 and CD8 counts, and for ART pharmacokinetics. Participants who have a viral load <50 copies/mL after completing 12 weeks of ATI (i.e., Week 60) and have not restarted ART have additional assessments performed at the Week 72 visit; specifically, blood sample collection for immunologic and virologic assays.

In Period 3 (Week 72 to Week 84), all participants who restart their ART during Period 2, whether during Period 2 or after completing Period 2 (i.e., at the Week 72 visit), have the viral load monitored at 4 and 12 weeks after restarting ART (Week 76 and Week 84). Participants have an end-of-study visit at Week 84. The Week 84 visit also serves as the Early Termination visit for participants who prematurely discontinue from the study during Period 3.

The efficacy endpoints is assessed by HIV-1 pVL changes over time along with peripheral and gut-associated lymphoid tissue (GALT) changes in viral reservoir. Participants are monitored for viremia throughout the study.

Blood samples collected for assessing HIV-1 pVL are used for determining virologic control of the virus and viral rebound., e.g., a viral load <50 copies/mL, or <2000 copies/mL. Sustained virologic control is generally <50 copies/mL during the ATI (Period 2, from Week 48 though Week 72).

The immunogenicity and pharmacodynamic endpoints are assessed based on following laboratory tests: (1) interferon-γ ELISPOT assay for determining de novo T cell responses to HIV vaccine-targeted regions of HIV-1 protein and the breadth and magnitude of total vaccine-induced HIV-1-specific responses, (2) changes in the following from before dosing of the compound of Formula (I) to 24 hours after compound dosing: (a) serum/plasma cytokines, (b) gene expression (including interferon-stimulated genes) in whole blood, (c) immune cell phenotype/activation in peripheral blood, (3) microbiome based on stool sample collection, and (4) changes in baseline GALT immune cell phenotype/activation, gene expression (including interferon-stimulated genes), HIV-1 specific T cell responses, and HIV-1 reservoir.

Stool samples are collected at Week 0 and Week 26, as well as upon early termination of the protocol, if applicable, for microbiome analysis.

Example 2. Dosing of an HIV Patient

A 40-year-old human male patient having a confirmed HIV-1 infection and receiving ART is administered the HIV vaccine and the compound of Formula (I) according to Example 1, thus treating the HIV-1 infection.

X. Sequences

In addition to sequences disclosed elsewhere in the present disclosures, the following sequences are provided as they are mentioned or used in various exemplary embodiments of the disclosures, which are provided for the purpose of illustration.

| SEQ ID NO | Sequence | Description |
|---|---|---|
| 1 | EKIRLRPGGKKKYKLKHIVWASRELERFAVNPGLLETSEGCRQILGQLQPSLQTGSEEL KSLYNTVATLYCVHQKIEV | HIV-1 p17 17-94 |
| 2 | KAFSPEVIPMFSAL | HIV-1 p24 30-43 |
| 3 | GHQAAMQMLKE | HIV-1 p24 61-71 |
| 4 | IAPGQMREPRGSDIAGTTSTLQEQIGWMTNNPPIPVGEIYKRWIILGLNKIVRMYSPTS I | HIV-1 p24 91-150 |
| 5 | YVDRFYKTLRAEQA | HIV-1 p24 164-177 |
| 6 | ACQGVGGPGHKARVL | HIV-1 p24 217-231 |
| 7 | CIERQANFLGKIWPSHKGRPGNFLQSR | HIV-1 p2p7p1p6 63-89 |
| 8 | KMIGGIGGFIKVRQYDQILIEICGHKAIGTVLVGPTPVNIIGRNLLTQIGCTLNF | HIV-1 protease 45-99 |
| 9 | LVEICITMEKEGKISKI | HIV-1 reverse transcriptase 34-50 |
| 10 | LRWGFTTPDKKHQKEPPFLWMGYELHPDKWTVQPIVLPEKDSWTVNDIQKLVGKL | HIV-1 reverse transcriptase 210-264 |

-continued

| SEQ ID NO | Sequence | Description |
|---|---|---|
| 11 | ILKEPVHGVYYDPSKDLIAEIQKQGQGQWTYQIY | HIV-1 reverse transcriptase 309-342 |
| 12 | TKELQKQITKIQNFRVYYRDSRDPLWKGPAKLLW | HIV-1 integrase 210-243 |
| 13 | KIIRDYGKQMAGDDCVA | HIV-1 integrase 266-282 |
| 14 | VKHHMYISKKAKGWFYRHHYESTHPR | HIV-1 Vif 25-50 |
| 15 | VTKLTEDRWNKPQKTKGHR | HIV-1 Vif 166-184 |
| 16 | AWLEAQEEEEVGF | HIV-1 Nef 56-68 |
| 17 | EKIRLRPGGKKKYKLKHIVWASRELERFAVNPGLLETSEGCRQILGQLQPSLQTGSEEL KSLYNTVATLYCVHQKIEVAAAKAFSPEVIPMFSALAAAGHQAAMQMLKEAAAIAPGQM REPRGSDIAGTTSTLQEQIGWMTNNPPIPVGEIYKRWIILGLNKIVRMYSPTSIAAAYV DRFYKTLRAEQAAACQGVGGPGHKARVLAAACTERQANFLGKIWPSHKGRPGNFLQSRA AAKMIGGIGGFIKVRQYDQILIEICGHKAIGTVLVGPTPVNIIGRNLLTQIGCTLNFAA ALVEICTEMEKEGKISKIAAALRWGFTTPDKKHQKEPPFLWMGYELHPDKWTVQPIVLP EKDSWTVNDIQKLVGKLAAAILKEPVHGVYYDPSKDLIAEIQKQGQGQWTYQIYAAATK ELQKQITKIQNFRVYYRDSRDPLWKGPAKLLWAAAKIIRDYGKQMAGDDCVAAAVKHHM YISKKAKGWFYRHHYESTHPRAAAVTKLTEDRWNKPQKTKGHRAAAWLEAQEEEEVGF | immunogenic polypeptide |
| 18 | GAGAAGATCCGCCTGCGCCCCGGCGGCAAGAAAAAGTACAAGCTGAAGCACATCGTGTG GGCCTCCCGCGAGCTGGAGCGCTTCGCCGTGAACCCCGGCCTGCTGGAGACCTCCGAGG GCTGCCGCCAGATCCTGGGCCAGCTGCAGCCCTCCCTGCAGACCGGCTCCGAGGAGCTG AAGTCCCTGTACAACACCGTGGCCACCCTGTACTGCGTGCACCAGAAGATCGAGGTGGC CGCCGCCAAGGCCTTCTCCCCCGAGGTGATCCCCATGTTCTCCGCCCTGGCCGCCGCCG GCCACCAGGCCGCCATGCAGATGCTGAAGGAGGCCGCCGCCATCGCCCCCGGCCAGATG CGCGAGCCCCGCGGCTCCGACATCGCCGGCACCACCTCCACCCTGCAGGAGCAGATCGG CTGGATGACCAACAACCCCCCCATCCCCGTGGGCGAGATCTACAAGCGCTGGATCATCC TGGGCCTGAACAAGATCGTGCGCATGTACTCCCCCACCTCCATCGCCGCCGCCTACGTG GACCGCTTCTACAAGACCCTGCGCGCCGAGCAGGCCGCCGCCTGCCAGGGCGTGGGCGG CCCCGGCCACAAGGCCCGCGTGCTGGCCGCCGCCTGCACCGAGCGCCAGGCCAACTTCC TGGGCAAGATCTGGCCCTCCCACAAGGGCCGCCCCGGCAACTTCCTGCAGTCCCGCGCC GCCGCCAAGATGATCGGCGGCATCGGCGGCTTCATCAAGGTGCGCCAGTACGACCAGAT CCTGATCGAGATCTGCGGCCACAAGGCCATCGGCACCGTGCTGGTGGGCCCCACCCCCG TGAACATCATCGGCCGCAACCTGCTGACCCAGATCGGCTGCACCCTGAACTTCGCCGCC CTGGTGGAGATCTGCACCGAGATGGAGAAGGAGGGCAAGATCTCCAAGATCGCCGCCGC CCTGCGCTGGGGCTTCACCACCCCCGACAAGAAGCACCAGAAGGAGCCCCCCTTCCTGT GGATGGGCTACGAGCTGCACCCCGACAAGTGGACCGTGCAGCCCATCGTGCTGCCCGAG AAGGACTCCTGGACCGTGAACGACATCCAGAAGCTGGTGGGCAAGCTGGCCGCCGCCAT CCTGAAGGAGCCCGTGCACGGCGTGTACTACGACCCCTCCAAGGACCTGATCGCCGAGA TCCAGAAGCAGGGCCAGGGCCAGTGGACCTACCAGATCTACGCCGCCGCCACCAAGGAG CTGCAGAAGCAGATCACCAAGATCCAGAACTTCCGCGTGTACTACCGCGACTCCCGCGA CCCCCTGTGGAAGGGCCCCGCCAAGCTGCTGTGGGCCGCCGCCAAGATCATCCGCGACT ACGGCAAGCAGATGGCCGGCGACGACTGCGTGGCCGCCGCCGTGAAGCACCACATGTAC ATCTCCAAGAAGGCCAAGGGCTGGTTCTACCGCCACCACTACGAGTCCACCCACCCCCG CGCCGCCGCCGTGACCAAGCTGACCGAGGACCGCTGGAACAAGCCCCAGAAGACCAAGG GCCACCGCGCCGCCGCCTGGCTGGAGGCCCAGGAGGAGGAGGAGGTGGGCTTCTGATAG | Nucleic acid encoding immunogenic polypeptide |

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating an HIV-1 infection in a human in need thereof suffering from HIV-1 infection, the method comprising administering to the human 6 mg of a compound of Formula (I):

(I)

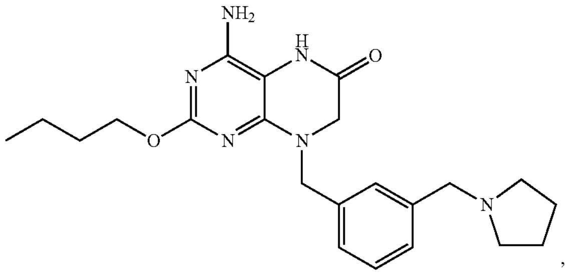

, and a first virus that is a replication-defective chimpanzee adenovirus comprising a nucleic acid encoding an immunogenic polypeptide comprising:

(i) a sequence having at least 90% sequence identity to SEQ ID NO: 1;

(ii) a sequence having at least 90% sequence identity to SEQ ID NO: 2;

(iii) a sequence having at least 90% sequence identity to SEQ ID NO: 3;

(iv) a sequence having at least 90% sequence identity to SEQ ID NO: 4;

(v) a sequence having at least 90% sequence identity to SEQ ID NO: 5;

(vi) a sequence having at least 90% sequence identity to SEQ ID NO: 6;

(vii) a sequence having at least 90% sequence identity to SEQ ID NO: 7;

(viii) a sequence having at least 90% sequence identity to SEQ ID NO: 8;

(ix) a sequence having at least 90% sequence identity to SEQ ID NO: 9;

(x) a sequence having at least 90% sequence identity to SEQ ID NO: 10;

a sequence having at least 90% sequence identity to SEQ ID NO: 11;

(xii) a sequence having at least 90% sequence identity to SEQ ID NO: 12;

(xiii) a sequence having at least 90% sequence identity to SEQ ID NO: 13;

(xiv) a sequence having at least 90% sequence identity to SEQ ID NO: 14;

(xv) a sequence having at least 90% sequence identity to SEQ ID NO: 15; and (xvi) a sequence having at least 90% sequence identity to SEQ ID NO: 16;

wherein at least two of (i) to (xvi) are joined by a single, dual, or triple alanine amino acid linker, wherein the linker results in the formation of an AAA sequence in the junction region between adjoining sequences, and wherein the sequence of each of (i) to (xvi) is 11-85 amino acids in length.

2. The method of claim 1, wherein the immunogenic polypeptide comprises:

(i) a sequence having at least 95% sequence identity to SEQ ID NO: 1;

(ii) a sequence having at least 95% sequence identity to SEQ ID NO: 2;

(iii) a sequence having at least 95% sequence identity to SEQ ID NO: 3;

(iv) a sequence having at least 95% sequence identity to SEQ ID NO: 4;

(v) a sequence having at least 95% sequence identity to SEQ ID NO: 5;

(vi) a sequence having at least 95% sequence identity to SEQ ID NO: 6;

(vii) a sequence having at least 95% sequence identity to SEQ ID NO: 7;

(viii) a sequence having at least 95% sequence identity to SEQ ID NO: 8;

(ix) a sequence having at least 95% sequence identity to SEQ ID NO: 9;

(x) a sequence having at least 95% sequence identity to SEQ ID NO: 10;

(xi) a sequence having at least 95% sequence identity to SEQ ID NO: 11;

(xii) a sequence having at least 95% sequence identity to SEQ ID NO: 12;

(xiii) a sequence having at least 95% sequence identity to SEQ ID NO: 13;

(xiv) a sequence having at least 95% sequence identity to SEQ ID NO: 14;

(XV) a sequence having at least 95% sequence identity to SEQ ID NO: 15; and (xvi) a sequence having at least 95% sequence identity to SEQ ID NO: 16.

3. The method of claim 1, wherein the immunogenic polypeptide comprises the sequences of SEQ ID NOS: 1-16, wherein at least two of SEQ ID NOS: 1-16 are joined by the single, dual, or triple alanine amino acid linker, and wherein the linker results in the formation of an AAA sequence in the junction region between adjoining sequences.

4. The method of claim 1, wherein the immunogenic polypeptide has an amino acid sequence according to SEQ ID NO: 17.

5. The method of claim 1, wherein the nucleic acid has a nucleic acid sequence according to SEQ ID NO: 18.

6. The method of claim 1, wherein the first virus comprises an Adenoviridae or a Poxviridae viral vector.

7. The method of claim 1, wherein the first virus comprises an adenovirus viral vector.

8. The method of claim 7, wherein the first virus is a chimpanzee adenovirus.

9. The method of claim 7, wherein $5\times10^{10}$ viral particles of the first virus is administered.

10. The method of claim 1, wherein the first virus is administered once every 12 weeks.

11. The method of claim 10, wherein the first virus is administered twice.

12. The method of claim 1, wherein the method further comprises administering a second virus comprising the nucleic acid encoding the immunogenic polypeptide.

13. The method of claim 12, wherein the second virus comprises a modified vaccinia virus Ankara (MVA) vector.

14. The method of claim 13, wherein $2\times10^{8}$ plaque-forming units of the second virus is administered.

15. The method of claim 12, wherein the second virus is administered once every 12 weeks.

16. The method of claim 15, wherein the second virus is administered twice.

17. The method of claim 12, wherein the first virus and the second virus are administered intramuscularly.

18. The method of claim 12, wherein the first virus is administered at Week 0 and Week 12, and the second virus is administered at Week 24 and Week 36.

19. The method of claim 1, wherein the compound of Formula (I) is administered every two weeks after the third administration of virus.

20. The method of claim 18, wherein the compound of Formula (I) is administered at Weeks 26, 28, 30, 32, 34, 38, 40, 42, 44, and 46.

21. The method of claim 1, wherein the human is virologically suppressed.

22. The method of claim 21, wherein the virologically suppressed human has a viral load of less than 200, 100, 50, or 20 copies of HIV-1 RNA per mL of plasma or blood.

23. The method of claim 21, wherein the virological suppression results from administration of anti-retroviral therapy.

24. The method of claim 23, wherein the anti-retroviral therapy comprises one or more agents selected from the group consisting of raltegravir, elvitegravir, soltegravir, cabotegravir, dolutegravir, abacavir, didanosine, tenofovir disoproxil fumarate, tenofovir alafenamide, emtricitabine, lamivudine, stavudine, zidovudine, abacavir, elvucitabine, tenofovir exalidex, festinavir, nevirapine, efavirenz, etravirine, rilpivirine, fosdevirine, doravirine, lersivirine, atazanavir, darunavir, indinavir, lopinavir, nelfinavir, saquinavir, tipranavir, ritonavir, fosamprenavir, maraviroc, enfuvirtide, fostemsavir, bevirimat, cobicistat, and bictegravir; or a pharmaceutically acceptable salt thereof.

25. A method of treating an HIV-1 infection in a virologically suppressed human in need thereof suffering from HIV-1 infection, the method comprising administering to the human a compound of Formula (I):

(I)

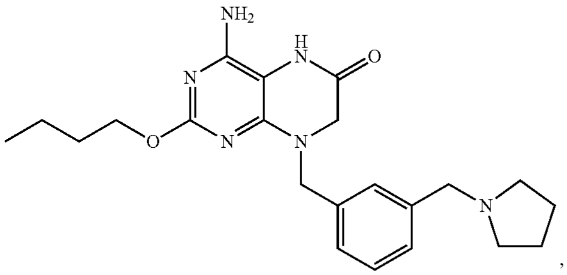

, a first virus comprising $5\times10^{10}$ viral particles of a replication-defective chimpanzee adenovirus comprising a nucleic acid encoding an immunogenic polypeptide having an amino acid sequence of SEQ ID NO: 17, and a second virus comprising $2\times10^{8}$ plaque-forming units of a modified vaccinia virus Ankara (MVA) comprising a nucleic acid encoding an immunogenic polypeptide having an amino acid sequence of SEQ ID NO: 17;

wherein the first virus is administered at Week 0 and Week 12, the second virus is administered at Week 24 and Week 36, 6 mg of the compound of Formula (I) is administered at Week 26 and Week 28, and 6 mg of the compound of Formula (I) is administered at Weeks 30, 32, 34, 38, 40, 42, 44, and 46.

* * * * *

SEQUENCE LISTING

```
<160> NUMBER OF SEQ ID NOS: 18

<210> SEQ ID NO 1
<211> LENGTH: 78
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p17 17-94

<400> SEQUENCE: 1

Glu Lys Ile Arg Leu Arg Pro Gly Gly Lys Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val
65                  70                  75


<210> SEQ ID NO 2
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p24 30-43

<400> SEQUENCE: 2

Lys Ala Phe Ser Pro Glu Val Ile Pro Met Phe Ser Ala Leu
1               5                   10


<210> SEQ ID NO 3
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p24 61-71

<400> SEQUENCE: 3

Gly His Gln Ala Ala Met Gln Met Leu Lys Glu
1               5                   10


<210> SEQ ID NO 4
<211> LENGTH: 60
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
```

<223> OTHER INFORMATION: HIV-1 p24 91-150

<400> SEQUENCE: 4

Ile Ala Pro Gly Gln Met Arg Glu Pro Arg Gly Ser Asp Ile Ala Gly
1 5 10 15

Thr Thr Ser Thr Leu Gln Glu Gln Ile Gly Trp Met Thr Asn Asn Pro
20 25 30

Pro Ile Pro Val Gly Glu Ile Tyr Lys Arg Trp Ile Ile Leu Gly Leu
35 40 45

Asn Lys Ile Val Arg Met Tyr Ser Pro Thr Ser Ile
50 55 60

<210> SEQ ID NO 5
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p24 164-177

<400> SEQUENCE: 5

Tyr Val Asp Arg Phe Tyr Lys Thr Leu Arg Ala Glu Gln Ala
1 5 10

<210> SEQ ID NO 6
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p24 217-231

<400> SEQUENCE: 6

Ala Cys Gln Gly Val Gly Gly Pro Gly His Lys Ala Arg Val Leu
1 5 10 15

<210> SEQ ID NO 7
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 p2p7p1p6 63-89

<400> SEQUENCE: 7

Cys Thr Glu Arg Gln Ala Asn Phe Leu Gly Lys Ile Trp Pro Ser His
1 5 10 15

Lys Gly Arg Pro Gly Asn Phe Leu Gln Ser Arg
20 25

<210> SEQ ID NO 8
<211> LENGTH: 55
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 protease 45-99

<400> SEQUENCE: 8

-continued

```
Lys Met Ile Gly Gly Ile Gly Gly Phe Ile Lys Val Arg Gln Tyr Asp
1               5                   10                  15

Gln Ile Leu Ile Glu Ile Cys Gly His Lys Ala Ile Gly Thr Val Leu
            20                  25                  30

Val Gly Pro Thr Pro Val Asn Ile Ile Gly Arg Asn Leu Leu Thr Gln
        35                  40                  45

Ile Gly Cys Thr Leu Asn Phe
    50                  55


<210> SEQ ID NO 9
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 reverse transcriptase 34-50

<400> SEQUENCE: 9

Leu Val Glu Ile Cys Thr Glu Met Glu Lys Glu Gly Lys Ile Ser Lys
1               5                   10                  15

Ile


<210> SEQ ID NO 10
<211> LENGTH: 55
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 reverse transcriptase 210-264

<400> SEQUENCE: 10

Leu Arg Trp Gly Phe Thr Thr Pro Asp Lys Lys His Gln Lys Glu Pro
1               5                   10                  15

Pro Phe Leu Trp Met Gly Tyr Glu Leu His Pro Asp Lys Trp Thr Val
            20                  25                  30

Gln Pro Ile Val Leu Pro Glu Lys Asp Ser Trp Thr Val Asn Asp Ile
        35                  40                  45

Gln Lys Leu Val Gly Lys Leu
    50                  55


<210> SEQ ID NO 11
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 reverse transcriptase 309-342

<400> SEQUENCE: 11

Ile Leu Lys Glu Pro Val His Gly Val Tyr Tyr Asp Pro Ser Lys Asp
1               5                   10                  15

Leu Ile Ala Glu Ile Gln Lys Gln Gly Gln Gly Gln Trp Thr Tyr Gln
            20                  25                  30

Ile Tyr


<210> SEQ ID NO 12
```

<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 integrase 210-243

<400> SEQUENCE: 12

```
Thr Lys Glu Leu Gln Lys Gln Ile Thr Lys Ile Gln Asn Phe Arg Val
1               5                   10                  15

Tyr Tyr Arg Asp Ser Arg Asp Pro Leu Trp Lys Gly Pro Ala Lys Leu
            20                  25                  30

Leu Trp
```

<210> SEQ ID NO 13
<211> LENGTH: 17
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 integrase 266-282

<400> SEQUENCE: 13

```
Lys Ile Ile Arg Asp Tyr Gly Lys Gln Met Ala Gly Asp Asp Cys Val
1               5                   10                  15

Ala
```

<210> SEQ ID NO 14
<211> LENGTH: 26
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 Vif 25-50

<400> SEQUENCE: 14

```
Val Lys His His Met Tyr Ile Ser Lys Lys Ala Lys Gly Trp Phe Tyr
1               5                   10                  15

Arg His His Tyr Glu Ser Thr His Pro Arg
            20                  25
```

<210> SEQ ID NO 15
<211> LENGTH: 19
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 Vif 166-184

<400> SEQUENCE: 15

```
Val Thr Lys Leu Thr Glu Asp Arg Trp Asn Lys Pro Gln Lys Thr Lys
1               5                   10                  15

Gly His Arg
```

<210> SEQ ID NO 16
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: HIV-1 Nef 56-68

<400> SEQUENCE: 16

```
Ala Trp Leu Glu Ala Gln Glu Glu Glu Glu Val Gly Phe
1               5                   10
```

<210> SEQ ID NO 17
<211> LENGTH: 530
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: immunogenic polypeptide

<400> SEQUENCE: 17

```
Glu Lys Ile Arg Leu Arg Pro Gly Gly Lys Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val Ala Ala
65                  70                  75                  80

Ala Lys Ala Phe Ser Pro Glu Val Ile Pro Met Phe Ser Ala Leu Ala
                85                  90                  95

Ala Ala Gly His Gln Ala Ala Met Gln Met Leu Lys Glu Ala Ala Ala
            100                 105                 110

Ile Ala Pro Gly Gln Met Arg Glu Pro Arg Gly Ser Asp Ile Ala Gly
        115                 120                 125

Thr Thr Ser Thr Leu Gln Glu Gln Ile Gly Trp Met Thr Asn Asn Pro
    130                 135                 140

Pro Ile Pro Val Gly Glu Ile Tyr Lys Arg Trp Ile Ile Leu Gly Leu
145                 150                 155                 160

Asn Lys Ile Val Arg Met Tyr Ser Pro Thr Ser Ile Ala Ala Ala Tyr
                165                 170                 175

Val Asp Arg Phe Tyr Lys Thr Leu Arg Ala Glu Gln Ala Ala Ala Cys
            180                 185                 190

Gln Gly Val Gly Gly Pro Gly His Lys Ala Arg Val Leu Ala Ala Ala
        195                 200                 205

Cys Thr Glu Arg Gln Ala Asn Phe Leu Gly Lys Ile Trp Pro Ser His
    210                 215                 220

Lys Gly Arg Pro Gly Asn Phe Leu Gln Ser Arg Ala Ala Ala Lys Met
225                 230                 235                 240

Ile Gly Gly Ile Gly Gly Phe Ile Lys Val Arg Gln Tyr Asp Gln Ile
                245                 250                 255

Leu Ile Glu Ile Cys Gly His Lys Ala Ile Gly Thr Val Leu Val Gly
            260                 265                 270

Pro Thr Pro Val Asn Ile Ile Gly Arg Asn Leu Leu Thr Gln Ile Gly
        275                 280                 285

Cys Thr Leu Asn Phe Ala Ala Ala Leu Val Glu Ile Cys Thr Glu Met
```

-continued 290 295 300

Glu Lys Glu Gly Lys Ile Ser Lys Ile Ala Ala Ala Leu Arg Trp Gly
305 310 315 320

Phe Thr Thr Pro Asp Lys Lys His Gln Lys Glu Pro Pro Phe Leu Trp
325 330 335

Met Gly Tyr Glu Leu His Pro Asp Lys Trp Thr Val Gln Pro Ile Val
340 345 350

Leu Pro Glu Lys Asp Ser Trp Thr Val Asn Asp Ile Gln Lys Leu Val
355 360 365

Gly Lys Leu Ala Ala Ala Ile Leu Lys Glu Pro Val His Gly Val Tyr
370 375 380

Tyr Asp Pro Ser Lys Asp Leu Ile Ala Glu Ile Gln Lys Gln Gly Gln
385 390 395 400

Gly Gln Trp Thr Tyr Gln Ile Tyr Ala Ala Ala Thr Lys Glu Leu Gln
405 410 415

Lys Gln Ile Thr Lys Ile Gln Asn Phe Arg Val Tyr Tyr Arg Asp Ser
420 425 430

Arg Asp Pro Leu Trp Lys Gly Pro Ala Lys Leu Leu Trp Ala Ala Ala
435 440 445

Lys Ile Ile Arg Asp Tyr Gly Lys Gln Met Ala Gly Asp Asp Cys Val
450 455 460

Ala Ala Ala Val Lys His His Met Tyr Ile Ser Lys Lys Ala Lys Gly
465 470 475 480

Trp Phe Tyr Arg His His Tyr Glu Ser Thr His Pro Arg Ala Ala Ala
485 490 495

Val Thr Lys Leu Thr Glu Asp Arg Trp Asn Lys Pro Gln Lys Thr Lys
500 505 510

Gly His Arg Ala Ala Ala Trp Leu Glu Ala Gln Glu Glu Glu Glu Val
515 520 525

Gly Phe
530

<210> SEQ ID NO 18
<211> LENGTH: 1593
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Nucleic acid encoding immunogenic polypeptide

<400> SEQUENCE: 18
gagaagatcc gcctgcgccc cggcggcaag aaaaagtaca agctgaagca catcgtgtgg 60
gcctcccgcg agctggagcg cttcgccgtg aaccccggcc tgctggagac ctccgagggc 120
tgccgccaga tcctgggcca gctgcagccc tccctgcaga ccggctccga ggagctgaag 180
tccctgtaca acaccgtggc caccctgtac tgcgtgcacc agaagatcga ggtggccgcc 240
gccaaggcct tctcccccga ggtgatcccc atgttctccg ccctggccgc cgccggccac 300
caggccgcca tgcagatgct gaaggaggcc gccgccatcg cccccggcca gatgcgcgag 360
ccccgcggct ccgacatcgc cggcaccacc tccaccctgc aggagcagat cggctggatg 420
accaacaacc cccccatccc cgtgggcgag atctacaagc gctggatcat cctgggcctg 480
aacaagatcg tgcgcatgta ctcccccacc tccatcgccg ccgcctacgt ggaccgcttc 540
tacaagaccc tgcgcgccga gcaggccgcc gcctgccagg gcgtgggcgg ccccggccac 600

-continued

```
aaggcccgcg tgctggccgc cgcctgcacc gagcgccagg ccaacttcct gggcaagatc    660
tggccctccc acaagggccg ccccggcaac ttcctgcagt cccgcgccgc cgccaagatg    720
atcggcggca tcggcggctt catcaaggtg cgccagtacg accagatcct gatcgagatc    780
tgcggccaca aggccatcgg caccgtgctg gtgggcccca cccccgtgaa catcatcggc    840
cgcaacctgc tgacccagat cggctgcacc ctgaacttcg ccgccctggt ggagatctgc    900
accgagatgg agaaggaggg caagatctcc aagatcgccg ccgccctgcg ctggggcttc    960
accacccccg acaagaagca ccagaaggag cccccccttcc tgtggatggg ctacgagctg   1020
cacccgaca agtggaccgt gcagcccatc gtgctgcccg agaaggactc ctggaccgtg    1080
aacgacatcc agaagctggt gggcaagctg gccgccgcca tcctgaagga gcccgtgcac   1140
ggcgtgtact acgacccctc caaggacctg atcgccgaga tccagaagca gggccagggc   1200
cagtggacct accagatcta cgccgccgcc accaaggagc tgcagaagca gatcaccaag   1260
atccagaact tccgcgtgta ctaccgcgac tcccgcgacc ccctgtggaa gggccccgcc   1320
aagctgctgt gggccgccgc caagatcatc cgcgactacg gcaagcagat ggccggcgac   1380
gactgcgtgg ccgccgccgt gaagcaccac atgtacatct ccaagaaggc caagggctgg   1440
ttctaccgcc accactacga gtccacccac ccccgcgccg ccgccgtgac caagctgacc   1500
gaggaccgct ggaacaagcc ccagaagacc aagggccacc gcgccgccgc ctggctggag   1560
gcccaggagg aggaagaggt gggcttctga tag                                 1593
```